United States Patent
Claremon et al.

(10) Patent No.: US 8,372,978 B2
(45) Date of Patent: Feb. 12, 2013

(54) SALTS OF METHYL 2-((R)-(3-CHLOROPHENYL)((R)-1-((S)-- (METHYLAMINO)-3-((R)-TETRAHYDRO-H-PYRAN-3-YL)PROPYLCARBAMOYL) IPERIDIN-3-YL)METHOXY)ETHYL ARBAMATE

(75) Inventors: David A. Claremon, Maple Glen, PA (US); Robert D. Simpson, Wilmington, DE (US); Lanqi Jia, Horsham, PA (US)

(73) Assignee: Vitae Pharmaceuticals, Inc., Fort Washington, PA (US)

( * ) Notice: Subject to any disclaimer, the term of this patent is extended or adjusted under 35 U.S.C. 154(b) by 186 days.

(21) Appl. No.: 12/851,267

(22) Filed: Aug. 5, 2010

(65) Prior Publication Data

US 2011/0098321 A1    Apr. 28, 2011

Related U.S. Application Data

(60) Provisional application No. 61/231,860, filed on Aug. 6, 2009.

(51) Int. Cl.
| | | |
|---|---|---|
| A61K 31/453 | (2006.01) | |
| C07D 413/12 | (2006.01) | |
| A61P 9/00 | (2006.01) | |

(52) U.S. Cl. ........................................ 546/207; 514/326
(58) Field of Classification Search .................. 546/207; 514/326
See application file for complete search history.

(56) References Cited

U.S. PATENT DOCUMENTS

| | | | |
|---|---|---|---|
| 3,071,618 | A | 1/1963 | Pinson et al. |
| 4,136,163 | A | 1/1979 | Watson et al. |
| 4,908,372 | A | 3/1990 | Carr et al. |
| 4,923,865 | A | 5/1990 | Cossement et al. |
| 5,218,002 | A | 6/1993 | Stroech et al. |
| 5,371,093 | A | 12/1994 | Carr et al. |
| 5,380,731 | A | 1/1995 | Carr et al. |
| 5,635,523 | A | 6/1997 | Kempf et al. |
| 5,767,144 | A | 6/1998 | Winn et al. |
| 6,162,927 | A | 12/2000 | Winn et al. |
| 6,323,368 | B1 | 11/2001 | Evans |
| 6,900,329 | B2 | 5/2005 | Clader et al. |
| 6,946,481 | B1 | 9/2005 | Winn et al. |
| 7,176,242 | B2 | 2/2007 | John et al. |
| 7,754,737 | B2 | 7/2010 | Baldwin et al. |
| 7,858,624 | B2 | 12/2010 | Baldwin et al. |
| 7,872,028 | B2 | 1/2011 | Baldwin et al. |
| 2004/0044201 | A1 | 3/2004 | Cummings et al. |
| 2007/0093492 | A1 | 4/2007 | Jiaang et al. |
| 2007/0265331 | A1 | 11/2007 | Decicco et al. |
| 2009/0018103 | A1 | 1/2009 | Baldwin et al. |
| 2009/0186884 | A1 | 7/2009 | Baldwin et al. |
| 2009/0312369 | A1 | 12/2009 | Baldwin et al. |
| 2009/0318501 | A1 | 12/2009 | Baldwin et al. |
| 2010/0160424 | A1 | 6/2010 | Baldwin et al. |
| 2010/0317697 | A1 | 12/2010 | Baldwin et al. |

FOREIGN PATENT DOCUMENTS

| | | |
|---|---|---|
| EP | 0178947 A2 | 4/1986 |
| EP | 1 882 684 A1 | 1/2008 |
| GB | 1351761 A | 5/1974 |
| JP | 51015098 A | 5/1976 |
| JP | 61100563 A | 5/1986 |
| JP | 01313467 | 12/1989 |
| JP | 2002/525361 A | 8/2002 |
| WO | WO 9604232 A1 | 2/1996 |
| WO | WO 98/54179 A1 | 12/1998 |
| WO | WO 99/54321 | 10/1999 |
| WO | WO 00/18744 A1 | 4/2000 |
| WO | WO 00/40558 | 7/2000 |
| WO | WO 00/63172 | 10/2000 |
| WO | WO 03/006423 A1 | 1/2003 |
| WO | WO 03/090690 | 11/2003 |
| WO | WO 2004/002483 | 1/2004 |
| WO | WO 2004/013098 | 2/2004 |
| WO | WO 2004/024675 | 3/2004 |
| WO | WO 2005/049027 | 6/2005 |
| WO | WO 2006/023844 | 3/2006 |
| WO | WO 2006/042150 A1 | 4/2006 |
| WO | WO 2007/070201 A1 | 6/2007 |
| WO | WO 2007/117557 | 10/2007 |
| WO | WO 2008/036216 A1 | 3/2008 |
| WO | WO 2008/036247 A1 | 3/2008 |
| WO | WO 2008/156817 | 12/2008 |
| WO | WO 2009/096996 | 8/2009 |
| WO | WO 2009/154766 | 12/2009 |
| WO | WO 2009/158377 | 12/2009 |

OTHER PUBLICATIONS

Database Beilstein XP002366304, Database Accession No. 7588231, 4-(2,2-dimethoxypropyl)-N-(2-hydroxyethyl) benzamide, vol. 108, No. 22, pp. 2800-2802 (1996).
Database Casreact, AN 90:168416, 1979.
Dorwald, F. Zaragoza, "Side Reactions in Organic Synthesis: A Guide to Successful Synthesis Design," Weinheim: Wiley-VCH Verlag GmbH & Co. KGaA, Preface p. ix, (2005).

(Continued)

Primary Examiner — San-Ming Hui
Assistant Examiner — Kathrien Cruz
(74) Attorney, Agent, or Firm — Hamilton, Brook, Smith & Reynolds, P.C.

(57) ABSTRACT

Mucic acid salts of a compound represented by the following structural formula:

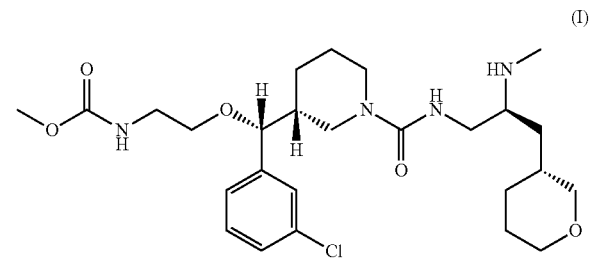

(I)

are disclosed. In particular, single crystalline mucic acid salts of the compound represented by structural formula (I) are characterized by a variety of properties and physical measurements. Methods of producing the mucic acid salts, using the salts to antagonize one or more aspartic proteases, and methods of treating a number of aspartic protease mediated disorders using the salts are described herein.

15 Claims, 14 Drawing Sheets

OTHER PUBLICATIONS

English Translation of Notification of the First Office Action, Chinese Patent Application No. 200580042064.7, Date of Notification May 8, 2009.
Examination Report from Gulf Cooperation Council Patent Office, GCC Application No. GCC/P/2006/7201, Dated Jul. 21, 2009.
Garrigues, B., et al., "Synthèse de 2-tert-butylthiophènes substitùes en position 5," *Bulletin De La Societe Chimique De France*, vol. 130, No. 1, pp. 58-63 (1993).
Jordan, V.Craig, "Tamoxifen: a Most Unlikely Pioneering Medicine," Nature Reviews: Durg Discovery, 2:205-213 (Mar. 2003).
Maibaum, J., et al., "Renin Inhibitors as Novel Treatments for Cardiovascular Disease," *Expert Opinion on Therapeutic Patents*, vol. 13, No. 5, pp. 589-603 (2003).
Moffett, R.B., "New Compounds with Possible Pharmacological Activity," *Journal of Chemical and Engineering Data*, vol. 25, No. 2, pp. 176-183 (1980).
Notice of Allowance from US Patent Office, U.S. Appl. No. 11/664,558, dated Mar. 1, 2010.
Notice of Allowance from US Patent Office, U.S. Appl. No. 12/225,985, dated Oct. 12, 2010.
Office Action from European Patent Office, European Application No. 07 838 310.6, Dated Sep. 2, 2009.
Office Action from European Patent Office, European Application No. 07 838 381.7, dated Oct. 16, 2009.
Office Action from European Patent Office, European Application No. 06 837 406.5, Dated Oct. 29, 2009.
Office Action from US Patent Office, U.S. Appl. No. 12/665,213, Dated Sep. 29, 2010.
Office Action from US Patent Office, U.S. Appl. No. 12/665,213, Dated Oct. 29, 2010.
Office Action from US Patent Office, U.S. Appl. No. 12/665,213, Dated Dec. 17, 2010.
Praly-Deprez, I., et al., "Synthesis of 11-amino-substituted-5,6-dimethy1-5$H$-pyrido[3',4':4,5]pyrrolo-[2,3-g]isoquinolines as New Ellipticine Analogues," *Journal of the Chemical Society*, Perkin Transactions 1., No. 12, pp. 3173-3175 (1991).
Rahuel, J. et al., "Structure-Based Drug Design: The Discovery of Novel Nonpeptide Orally Active Inhibitors of Human Renin," Chemistry & Biology, 7:493-504 (2000).
Schultz O.E., et al., "Pyridine and quinoline analogues of procaine and procainamide," *Arzneimittel-Forschung*, vol. 22, No. 7, pp. 1117-1120 (1972).
Shabat, D., et al., "Katalytische Antikorper als Sonden Fur die Evolution von Enzymen: Modellierung einer fruhen Glycosidase," *Angew. Chem.*, 108(22):2800-2802 (1996).
Stachel, S.J. et al., "Conformationally biased P3 amide replacements of beta-secretase inhibitors," Bioorganic & Med. Chem. Letters, 16(3):641-644 (2006).
Whitehead, C.W., "The Synthesis of 5-Carbethoxyuracils," *Journal of the American Chemical Society*, vol. 74, pp. 4267-4271 (1952).
Wood, J.N., et al., "Voltage-Gated Sodium Channels and Pain Pathways," *J. Neurobiol.*, 61:55-71 (2004).
International Search Report, International Application No. PCT/US2005/036230 (Feb. 20, 2006).
Written Opinion of the International Searching Authority, International Application No. PCT/US2005/036230 (Feb. 20, 2006).
Notification Concerning Transmittal of International Preliminary Report on Patentability, and International Preliminary Report on Patentability, International Application No. PCT/US2005/036230, mail date Apr. 19, 2007.
International Search Report, International Application No. PCT/US2006/043920 (Mar. 20, 2007).
Written Opinion of the International Searching Authority, International Application No. PCT/US2006/043920 (Mar. 20, 2007).
Notification Concerning Transmittal of International Preliminary Report on Patentability, and International Preliminary Report on Patentability, International Application No. PCT/US2006/043920, mail date May 22, 2008.
Written Opinion of the International Searching Authority, International Application No. PCT/US2007/008518 (Oct. 8, 2008).
International Search Report, International Application No. PCT/US2007/008518 (Oct. 8, 2008).
Notification Concerning Transmittal of International Preliminary Report on Patentability, and International Preliminary Report on Patentability, International Application No. PCT/US2007/008518, mail date Oct. 10, 2007.
International Search Report, International Application No. PCT/US2007/020164 (Dec. 28, 2007).
Written Opinion of the International Searching Authority, International Application No. PCT/US2007/020164 (Dec. 28, 2007).
Notification Concerning Transmittal of International Preliminary Report on Patentability, and International Preliminary Report on Patentability, International Application No. PCT/US2007/020164, Date of Mailing Apr. 2, 2009.
International Search Report, International Application No. PCT/US2007/020086 (Feb. 5, 2008).
Written Opinion of the International Searching Authority, International Application No. PCT/US2007/020086 (Feb. 5, 2008).
Notification Concerning Transmittal of International Preliminary Report on Patentability, and International Preliminary Report on Patentability, International Application No. PCT/US2007/020086, Date of Mailing Apr. 2, 2009.
International Search Report, International Application No. PCT/US2008/007662 (Apr. 21, 2009).
Written Opinion of the International Searching Authority, International Application No. PCT/US2008/007662 (Apr. 21, 2009).
Notification Concerning Transmittal of International Preliminary Report on Patentability, and International Preliminary Report on Patentability, International Application No. PCT/US2008/007662, mail date Jan. 7, 2010.
Written Opinion of the International Searching Authority, International Application No. PCT/US08/67650, Date of Mailing Jun. 22, 2009.
International Search Report, International Application No. PCT/US08/67650, Date of Mailing Jun. 22, 2009.
Notification Concerning Transmittal of International Preliminary Report on Patentability, and International Preliminary Report on Patentability, International Application No. PCT/US2008/067650, mail date Jan. 7, 2010.
International Search Report, International Application No. PCT/US2009/48389 (Sep. 11, 2009).
Written Opinion of the International Searching Authority, International Application No. PCT/US2009/48389 (Sep. 11, 2009).
Notification Concerning Transmittal of International Preliminary Report on Patentability, and International Preliminary Report on Patentability, International Application No. PCT/US2009/48389, mail date Jan. 13, 2011.
International Search Report, International Application No. PCT/US2009/003650 (Oct. 9, 2009).
Written Opinion of the International Searching Authority, International Application No. PCT/US2009/003650 (Oct. 9, 2009).
Notification Concerning Transmittal of International Preliminary Report on Patentability, and International Preliminary Report on Patentability, International Application No. PCT/US2009/003650, mail date Dec. 21, 2010.
International Search Report and Written Opinion of the International Searching Authority, International Application No. PCT/US2010/044568 (Nov. 8, 2010).
Bhanuprakash K., et al., "Computational Design of New Cyclic Urea Inhibitors for Improved Binding of HIV-1 Aspartic Protease," *Biochemical and Biophysical Research Communications*, 268(2): 384-389 (2000).
Restriction Requirement from U.S. Patent Office, U.S. Appl. No. 12/311,020, Dated: Jun. 3, 2011.
Restriction Requirement from U.S. Patent Office, U.S. Appl. No. 12/311,012, Dated: Jun. 24, 2011.
Restriction Requirement Office Action from U.S. Patent Office, U.S. Appl. No. 12/665,213, Dated: Jun. 24, 2011.
Office Action from U.S. Patent Office, U.S. Appl. No. 12/311,012, Dated: Aug. 22, 2011.
Office Action from U.S. Patent Office, U.S. Appl. No. 12/311,020, Dated: Aug. 23, 2011.

Notice of Allowance and Fees Due, U.S. Appl. No. 12/665,213, filed Feb. 19, 2010, Date of Notice: Feb. 10, 2012.

Notification Concerning Transmittal of International Preliminary Report on Patentability, International ApplicationNo. PCT/US2010/044568, International Filing Date: Aug. 5, 2010, Date of Mailing: Feb. 16, 2012.

Hammond, et al., "Preparation of phenyloxymethylbenzamide derivatives for use as aspartic protease inhibitors," AN 2009:1589830; DN 152:74734, CAPLUS [online],[Retrieved on Mar. 16, 2012]. Retrieved from the Internet URL: https://stnweb.cas.org/cgi-bin/sdcgi?SID=753964-0147118521-200&APP=stnweb&.

Notice of Allowance and Fees Due, U.S. Appl. No. 12/311,012, filed Jul. 14, 2009, Date of Notice: Feb. 14, 2012.

Office Communication, U.S. Appl No. 12/802,142, filed May 28, 2010, Date of Communication: Mar. 19, 2012.

Office Communication, U.S. Appl. No. 12/084,928, filed Nov. 5, 2009, Date of Communication: Mar. 5, 2012.

SALTS OF METHYL 2-((R)-(3-CHLOROPHENYL)((R)-1-((S)--(METHYLAMINO)-3-((R)-TETRAHYDRO-H-PYRAN-3-YL)PROPYLCARBAMOYL)IPERIDIN-3-YL)METHOXY)ETHYL ARBAMATE

RELATED APPLICATION(S)

This application claims the benefit of U.S. Provisional Application No. 61/231,860, filed on Aug. 6, 2009.

The entire teachings of the above application are incorporated herein by reference.

BACKGROUND OF THE INVENTION

International Publication Number WO 2008/036247 describes a series of compounds which are indicated as having inhibitory activity against aspartic proteases, particularly renin, and which are indicated as being useful in the treatment of aspartic protease mediated disorders. Methyl 2-((R)-(3-chlorophenyl)((R)-1-((S)-2-(methylamino)-3-((R)-tetrahydro-2H-pyran-3-yl)propylcarbamoyl)piperidin-3-yl)methoxy)ethylcarbamate, structurally represented by Formula I,

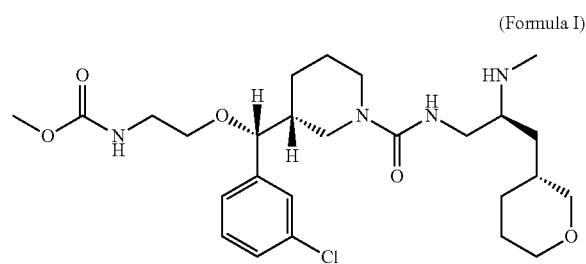 [SMILES: CN[C@H](CNC(=O)N1CCC[C@@H]([C@@H](OCCNC(=O)OC)c2cccc(Cl)c2)C1)C[C@H]1CCCOC1]

(Formula I)

is one of the compounds disclosed in WO 2008/036247. WO 2008/036247 further discloses the pamoate salt (2:1) of the compound represented by structural formula (I), and describes the use of the trifluoroacetic acid salt for isolation purposes but not for crystallization.

Although the 2:1 pamoate salt of the compound represented by structural formula (I) was obtained in good yield and was highly crystalline, the desired bioavailability and water solubility was not achieved.

There is a need for salt forms of the compound represented by structural formula (I) that are crystalline, have good aqueous solubility, good in vivo oral bioavailability, and otherwise have physical properties that are amenable to large scale manufacture.

SUMMARY OF THE INVENTION

It has been found that the mucic acid salt of the compound represented by structural formula (I) (hereinafter "Formula (I) Mucic Acid Salt") can be formed under specific conditions to provide certain sufficiently non-hygroscopic crystalline forms, in particular, single crystalline forms Form B, Form C and Form D. These crystalline forms of Formula (I) Mucic Acid Salt have been found to have advantageous properties when compared to other salts of Formula (I), and even when compared to other crystalline forms of Formula (I) Mucic Acid Salt, specifically, Form A and Form E. Other acids which were used in an attempt to prepare desirable salt forms of the compound represented by Formula (I) included: hydrochloric acid, sulfuric acid, phosphoric acid, acetic acid, adipic acid, L-aspartic acid, benzoic acid, camphoric acid, citric acid, fumaric acid, gentisic acid, L-glutamic acid, glutaric acid, glycolic acid, hippuric acid, 1-hydroxy-2-naphthoic acid, α-ketoglutaric acid, lactobionic acid, maleic acid, D-malic acid, L-malic acid, malonic acid, DL-mandelic acid, 1,5-naphthalenedisulfonic acid, nicotinic acid, orotic acid, propionic acid, L-pyroglutamic acid, succinic acid, and D- and L-tartaric acid. However, use of any of these acids for the preparation of a salt form of the compound of Formula (I) has been found to have disadvantages relating to one or more of (i) failure to provide crystalline salts under the conditions employed, (ii) failure to provide crystalline salts in sufficient quantities and/or yields to warrant further consideration under the conditions employed, (iii) failure to provide sufficiently non-hygroscopic salts, and (iv) failure to provide an acid salt with sufficient bioavailability. Furthermore, it is preferred that the acid is Generally Recognized as Safe (GRAS). More preferably the acid belongs to FDA Class I.

In addition to being sufficiently non-hygroscopic, certain crystalline forms of Formula (I) Mucic Acid Salt, in particular, single crystalline forms Form B, Form C and Form D have good aqueous solubility, and good in vivo oral bioavailability. These are favorable properties for large scale manufacture and render Formula (I) Mucic Acid Salt an attractive drug candidate.

One embodiment of the present invention is a crystalline form of the mucic acid salt of the compound represented by Structural Formula (I), wherein the crystalline form is selected from Form B, Form C, Form D or a combination thereof.

A related embodiment of the invention is to the mucic acid salt of the compound represented by Formula (I). As noted above, the mucic acid salt of the compound represented by Formula (I) is referred to herein as "Formula (I) Mucic Acid Salt." The compound represented by Formula (I) is referred to herein as "Formula (I) Free Base."

Another embodiment of the invention is a pharmaceutical composition comprising a pharmaceutically acceptable carrier or diluent and Formula (I) Mucic Acid Salt.

Another embodiment of the invention is a method of antagonizing one or more aspartic proteases in a subject in need thereof, comprising administering to the subject an effective amount of Formula (I) Mucic Acid Salt.

Another embodiment of the invention is a method for treating an aspartic protease mediated disorder in a subject comprising administering to the subject an effective amount of Formula (I) Mucic Acid Salt.

DETAILED DESCRIPTION OF THE INVENTION

The present invention provides unique crystalline forms of Formula (I) Mucic Acid Salt and new pharmaceutical compositions of Formula (I) Mucic Acid Salt comprising crystalline forms of Formula (I) Mucic Acid Salt described herein. The present invention also provides methods of antagonizing one or more aspartic proteases in a subject in need thereof, comprising administering to the subject an effective amount of Formula (I) Mucic Acid Salt including crystalline forms of Formula (I) Mucic Acid Salt described herein. The present invention also provides methods for treating an aspartic protease mediated disorder in a subject comprising administering to the subject an effective amount of Formula (I) Mucic Acid Salt including crystalline forms of Formula (I) Mucic Acid Salt described herein. Additionally, the present invention provides methods for preparing specific crystalline forms of Formula (I) Mucic Acid Salt.

One embodiment of the present invention is Formula (I) Mucic Acid Salt.

A more particular embodiment is a crystalline form of Formula (I) Mucic Acid Salt.

Another more particular embodiment is a crystalline form of Formula (I) Mucic Acid Salt, wherein the crystalline form is selected from Form B, Form C, Form D or a combination thereof.

In another more particular embodiment, the Formula (I) Mucic Acid Salt is a hemi mucate salt.

In another particular embodiment of the invention, at least a particular percentage by weight of Formula (I) Mucic Acid Salt is crystalline. Particular weight percentages include 50%, 70%, 72%, 75%, 77%, 80%, 82%, 85%, 86%, 87%, 88%, 89%, 90%, 91%, 92%, 93%, 94%, 95%, 96%, 97%, 98%, 99%, 99.5%, 99.9%, a percentage between 50% and 100%, or a percentage between 70% and 100%.

In another particular embodiment of the invention, at least a particular percentage by weight of a crystalline form of Formula (I) Mucic Acid Salt is a single crystalline form of Formula (I) Mucic Acid Salt. Particular weight percentages include 50%, 70%, 72%, 75%, 77%, 80%, 82%, 85%, 86%, 87%, 88%, 89%, 90%, 91%, 92%, 93%, 94%, 95%, 96%, 97%, 98%, 99%, 99.5%, 99.9%, a percentage between 50% and 100%, or a percentage between 70% and 100%.

Figure 1:
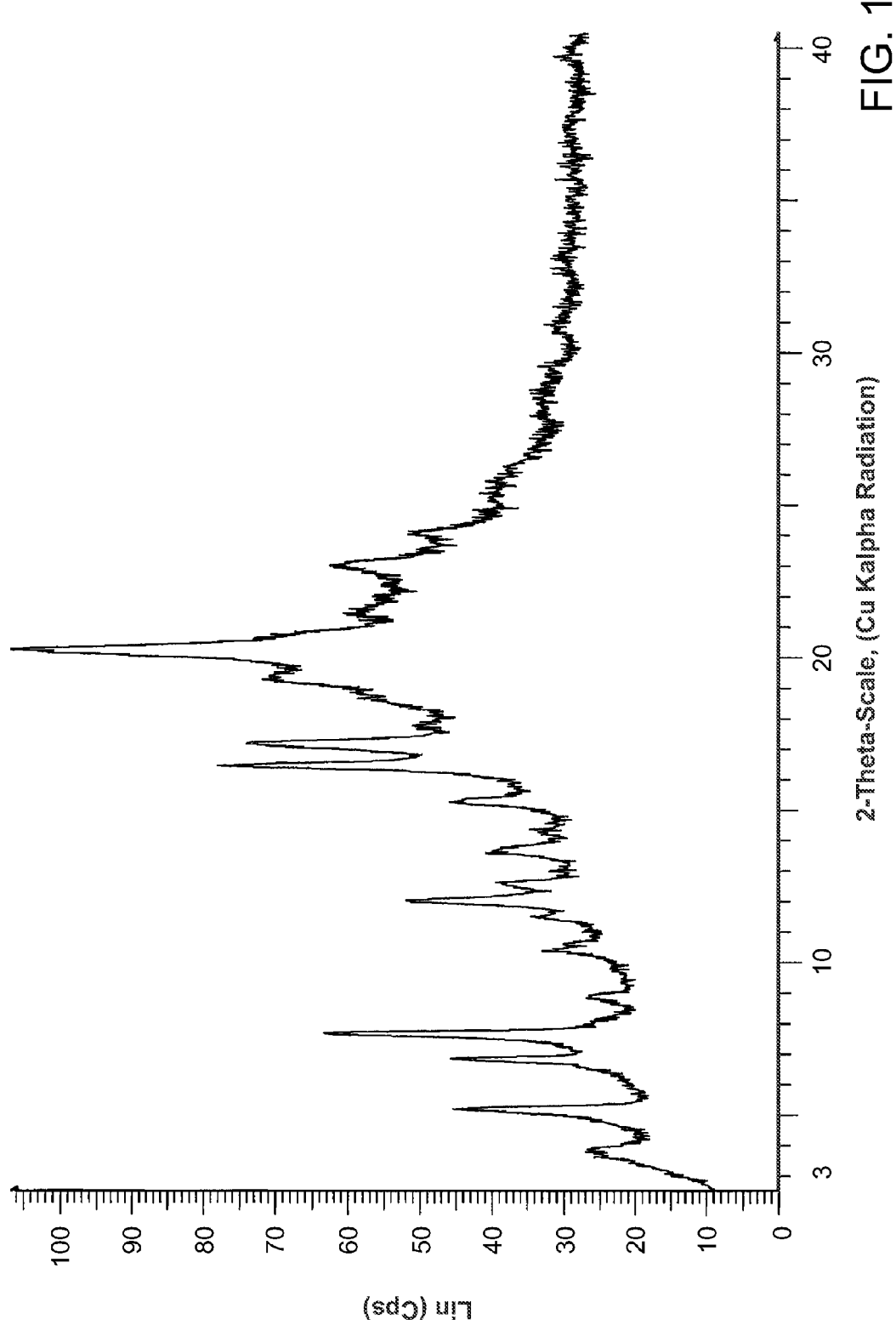
FIG. 1 shows an X-ray powder diffraction pattern of Formula (I) Mucic Acid Salt—Form B prepared as described in Example 3.
Figure 2:
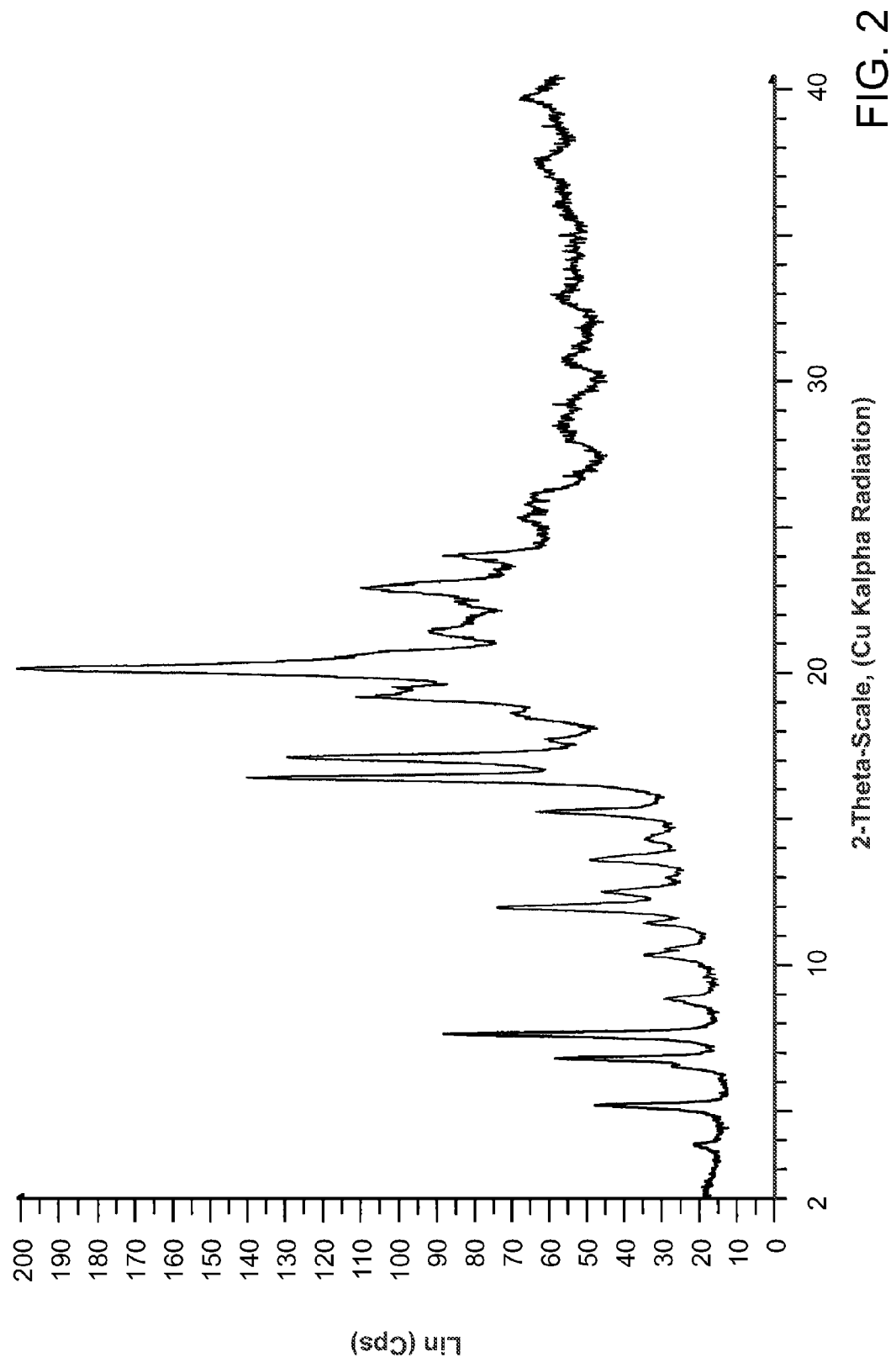
FIG. 2 shows an X-ray powder diffraction pattern of Formula (I) Mucic Acid Salt—Form B prepared as described in Example 4.

Another embodiment of the present invention is directed to a crystalline form of Formula (I) Mucic Acid Salt, providing an X-ray powder diffraction pattern substantially in accordance with FIG. 1 and/or FIG. 2.

Figure 3:
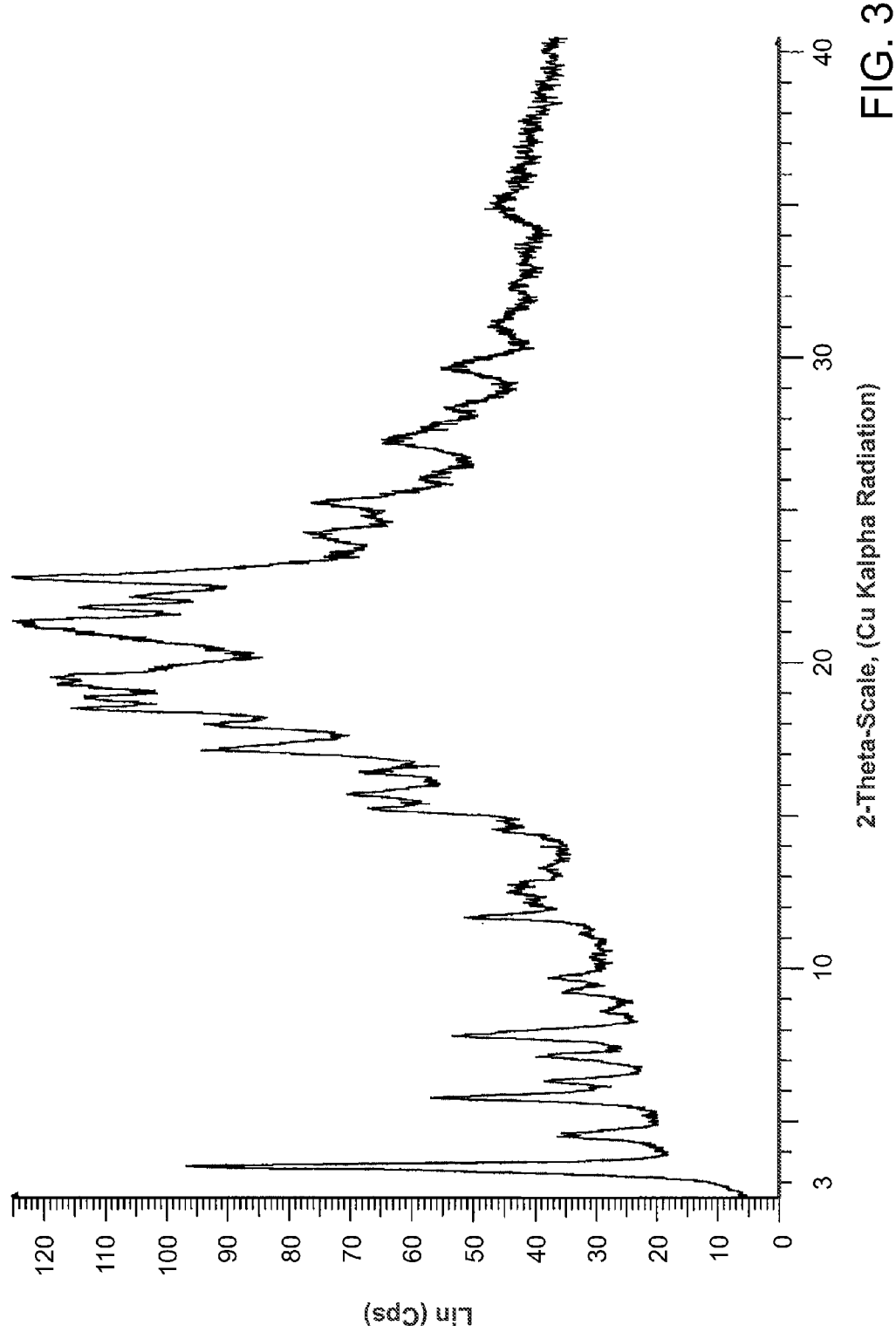
FIG. 3 shows an X-ray powder diffraction pattern of Formula (I) Mucic Acid Salt—Form C prepared as described in Example 5.

Another embodiment of the present invention is directed to a crystalline form of Formula (I) Mucic Acid Salt, providing an X-ray powder diffraction pattern substantially in accordance with FIG. 3.

Figure 4:
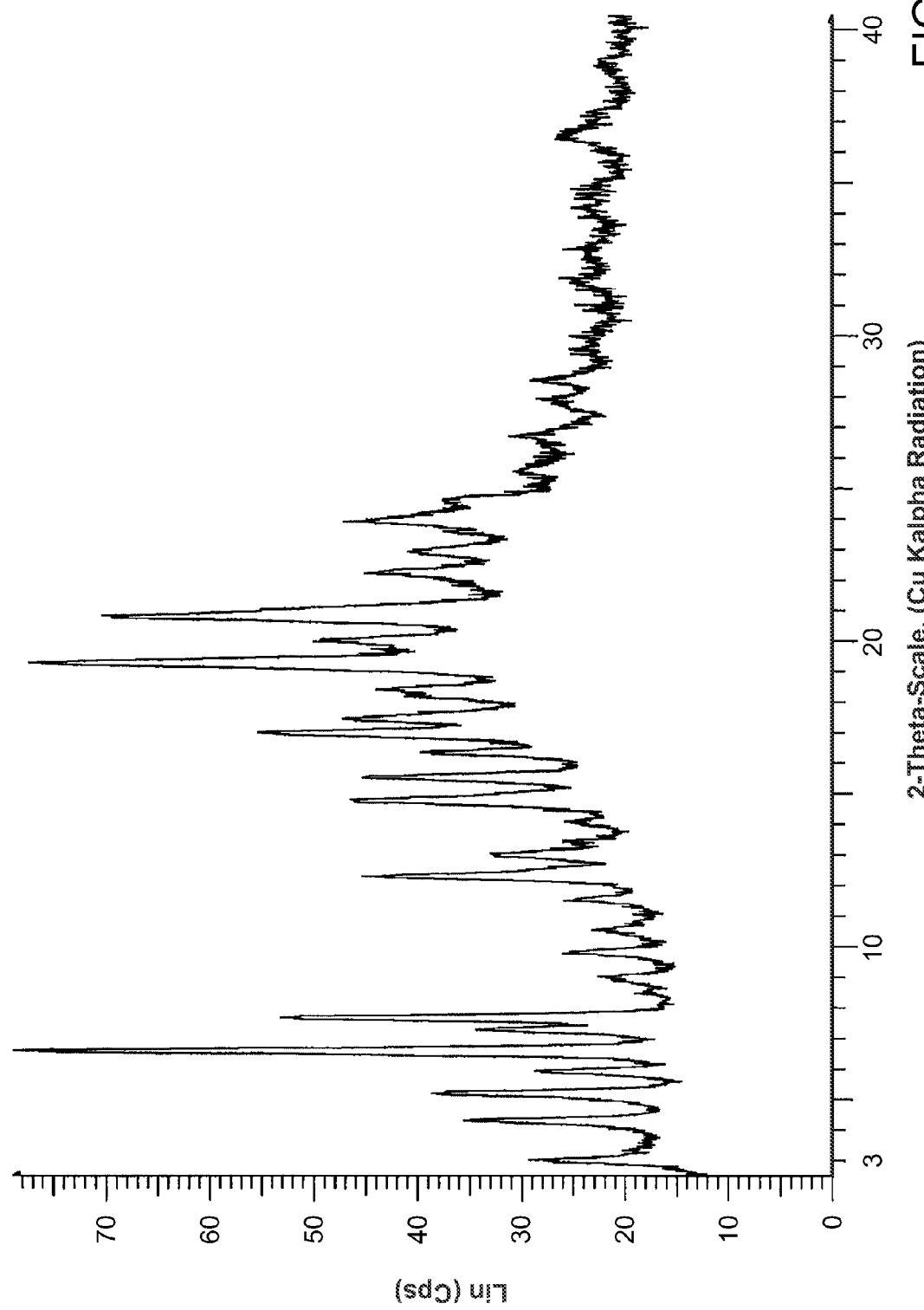
FIG. 4 shows an X-ray powder diffraction pattern of Formula (I) Mucic Acid Salt—Form D prepared as described in Example 6.

Another embodiment of the present invention is directed to a crystalline form of Formula (I) Mucic Acid Salt, providing an X-ray powder diffraction pattern substantially in accordance with FIG. 4.

Figure 5:
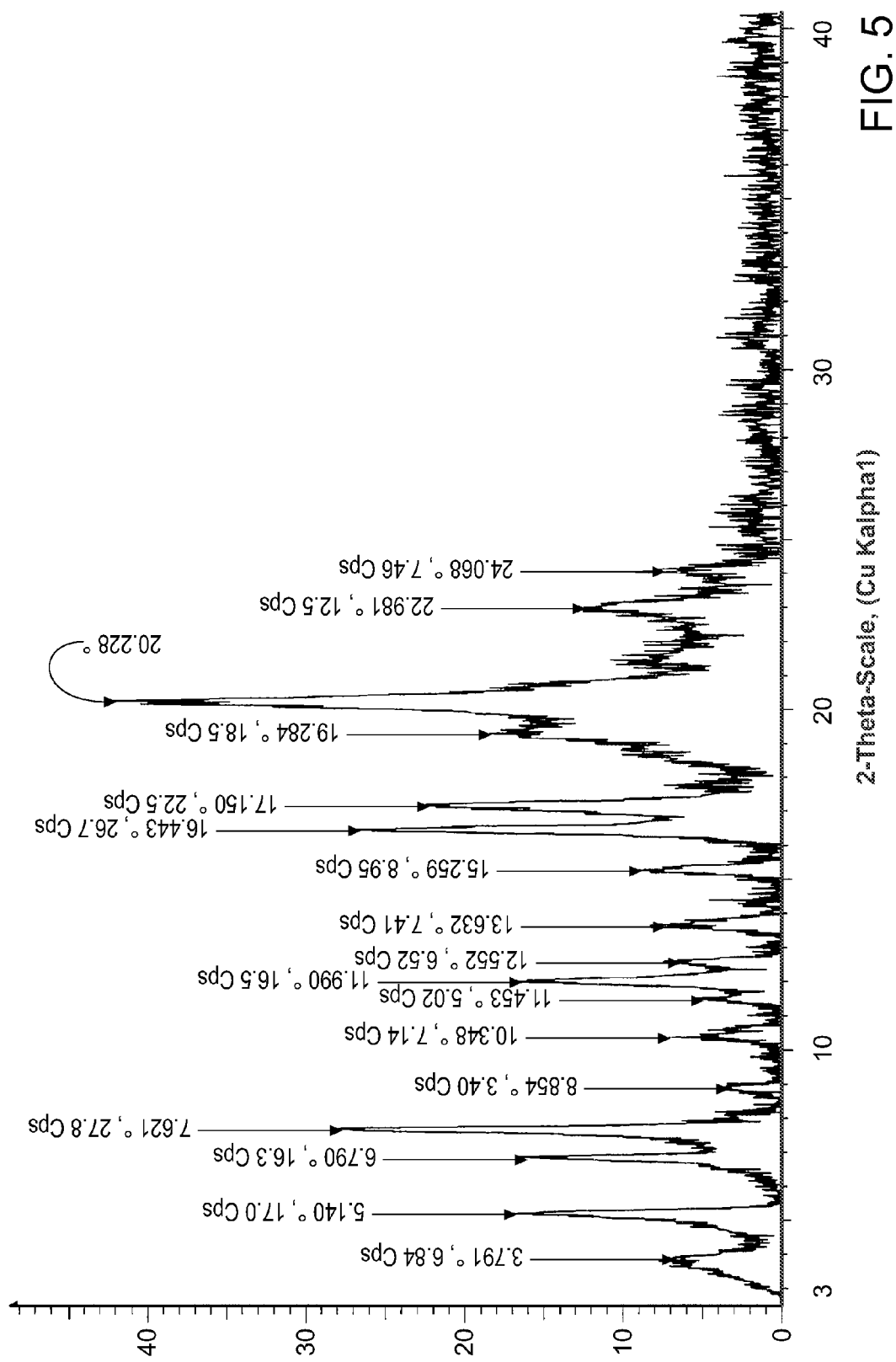
FIG. 5 shows an X-ray powder diffraction pattern of Formula (I) Mucic Acid Salt—Form B. The data was processed to remove amorphous background from the diffractogram shown in FIG. 1.
Figure 6:
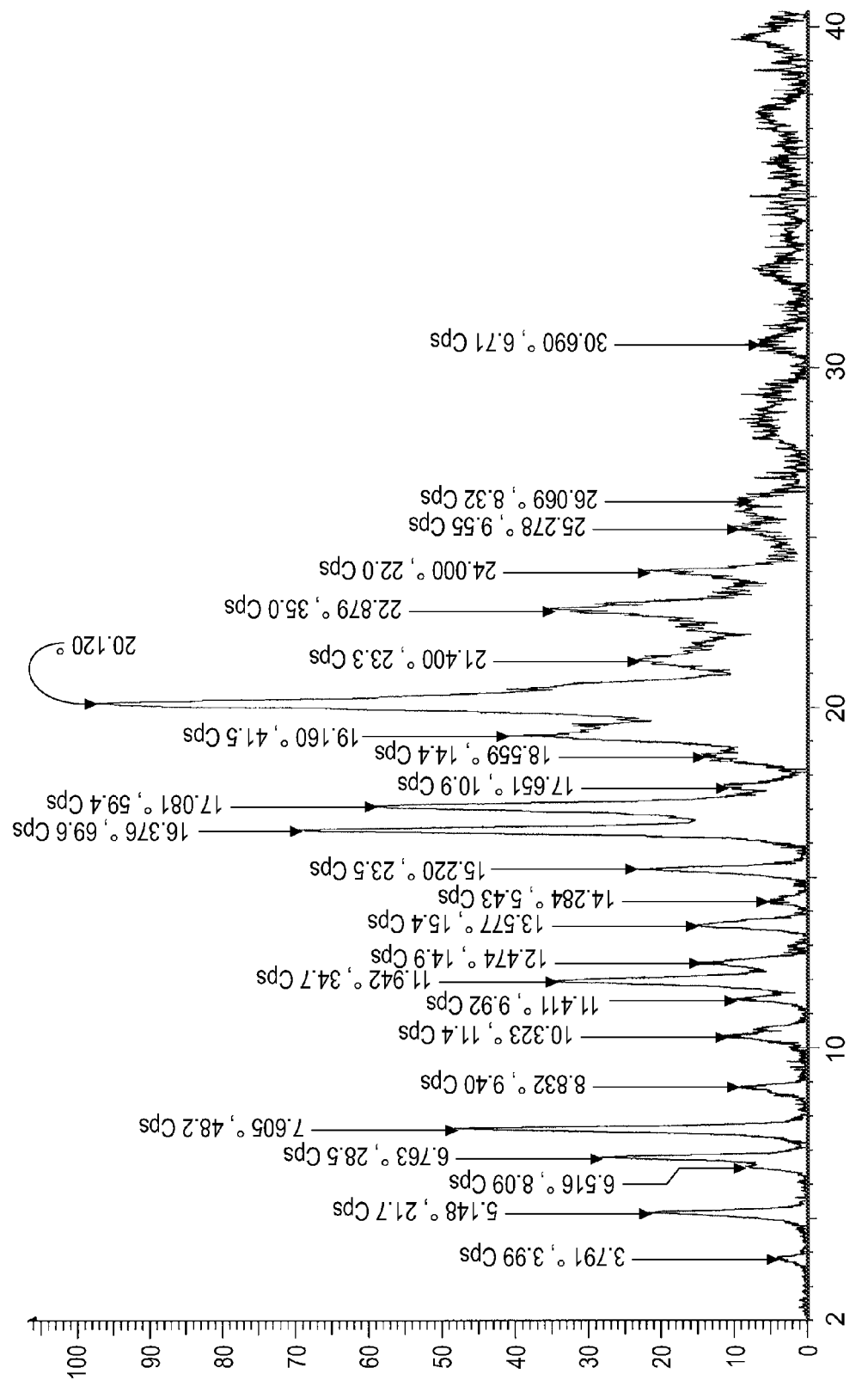
FIG. 6 shows an X-ray powder diffraction pattern of Formula (I) Mucic Acid Salt—Form B. The data was processed to remove amorphous background from the diffractogram shown in FIG. 2.

Another embodiment of the present invention is directed to a crystalline form of Formula (I) Mucic Acid Salt, providing a processed X-ray powder diffraction pattern substantially in accordance with FIG. 5 and/or FIG. 6.

Figure 7:
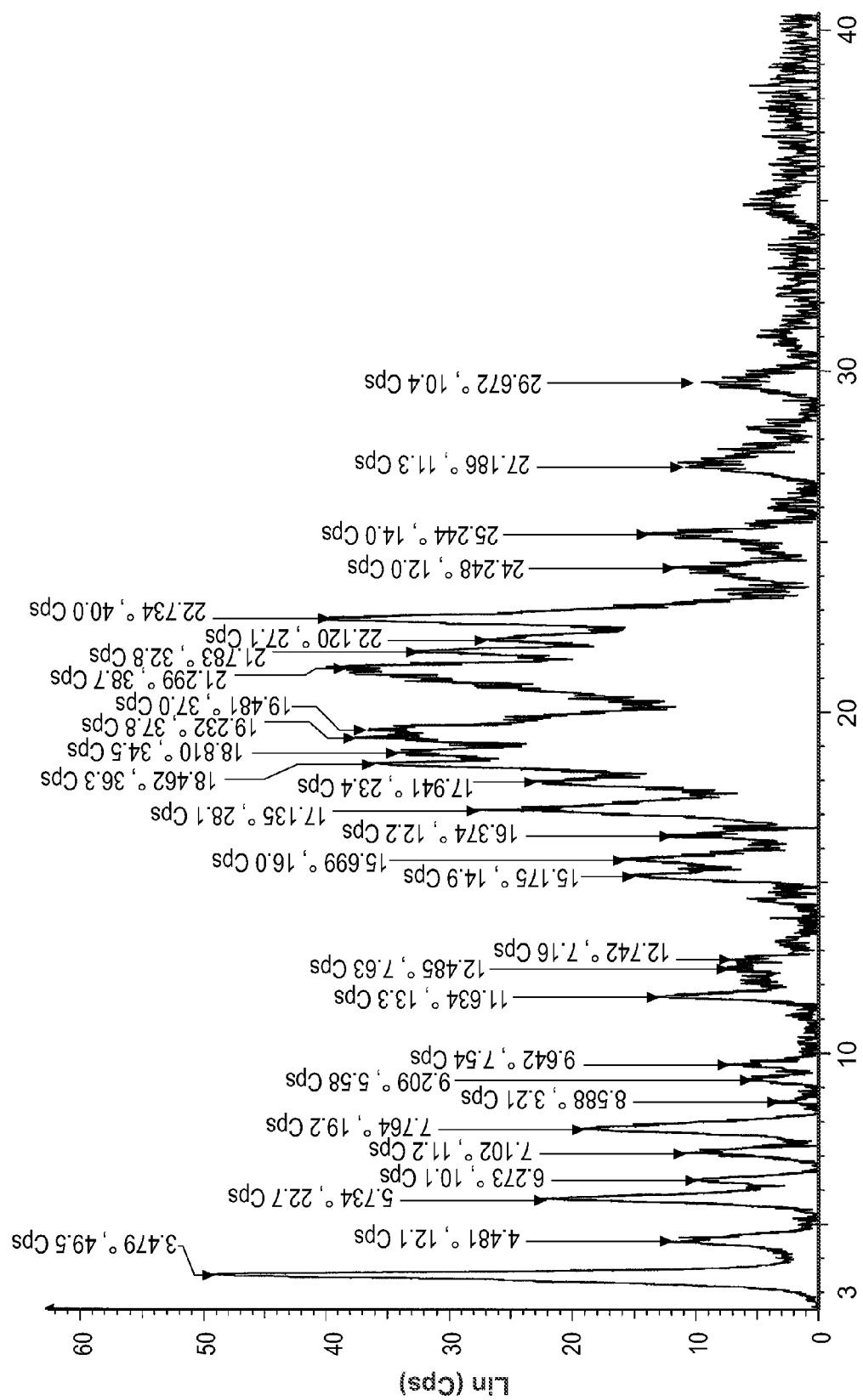
FIG. 7 shows an X-ray powder diffraction pattern of Formula (I) Mucic Acid Salt—Form C. The data was processed to remove amorphous background from the diffractogram shown in FIG. 3.

Another embodiment of the present invention is directed to a crystalline form of Formula (I) Mucic Acid Salt, providing a processed X-ray powder diffraction pattern substantially in accordance with FIG. 7.

Figure 8:
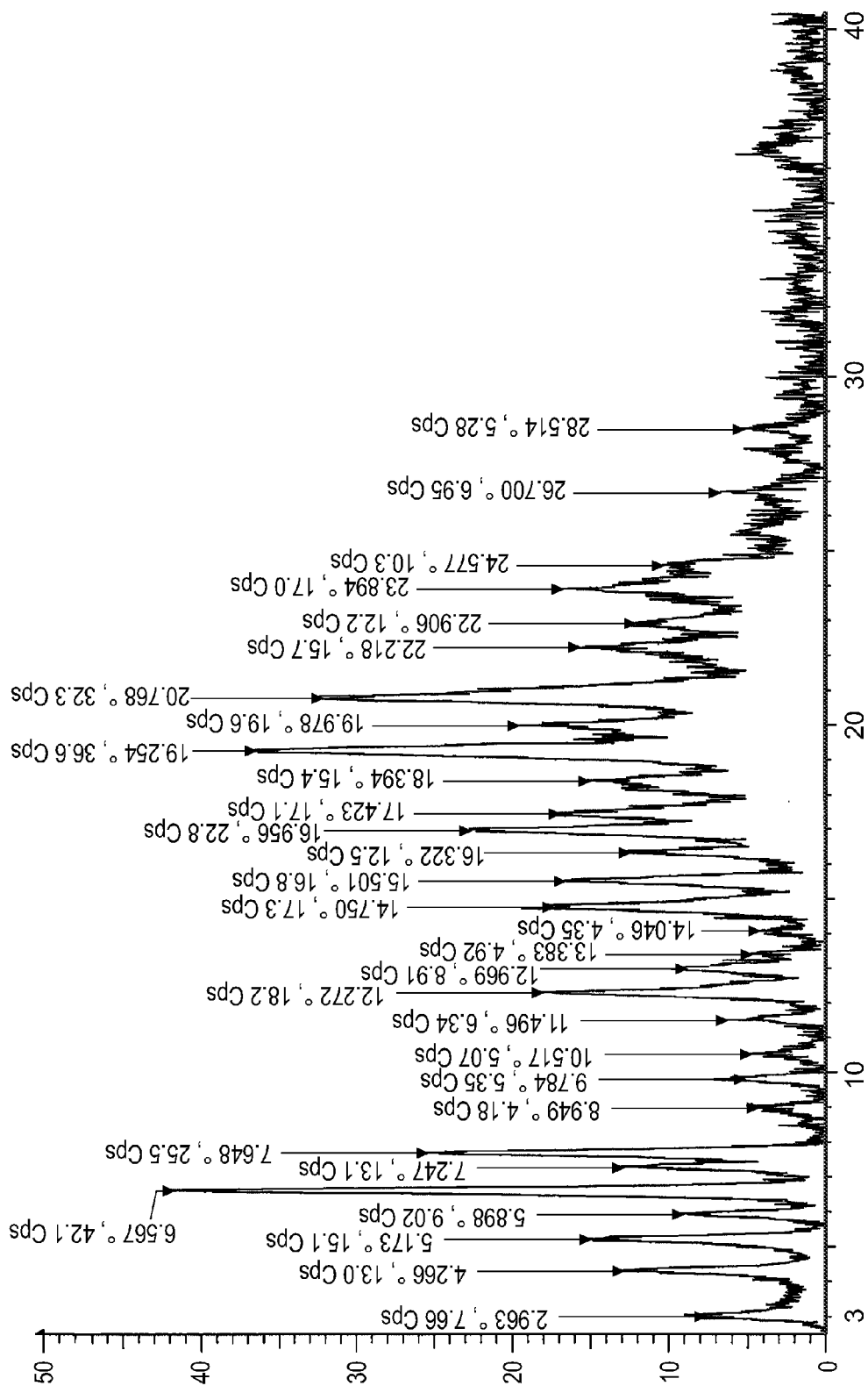
FIG. 8 shows an X-ray powder diffraction pattern of Formula (I) Mucic Acid Salt—Form D. The data was processed to remove amorphous background from the diffractogram shown in FIG. 4.

Another embodiment of the present invention is directed to a crystalline form of Formula (I) Mucic Acid Salt, providing a processed X-ray powder diffraction pattern substantially in accordance with FIG. 8.

Another embodiment of the present invention is directed to a crystalline form of Formula (I) Mucic Acid Salt, providing an X-ray powder diffraction pattern substantially in accordance with FIG. 1 and/or FIG. 2, and a processed X-ray powder diffraction pattern substantially in accordance with FIG. 5 and/or FIG. 6.

Another embodiment of the present invention is directed to a crystalline form of Formula (I) Mucic Acid Salt, providing an X-ray powder diffraction pattern substantially in accordance with FIG. 3, and a processed X-ray powder diffraction pattern substantially in accordance with FIG. 7.

Another embodiment of the present invention is directed to a crystalline form of Formula (I) Mucic Acid Salt, providing an X-ray powder diffraction pattern substantially in accordance with FIG. 4, and a processed X-ray powder diffraction pattern substantially in accordance with FIG. 8.

Figure 9:
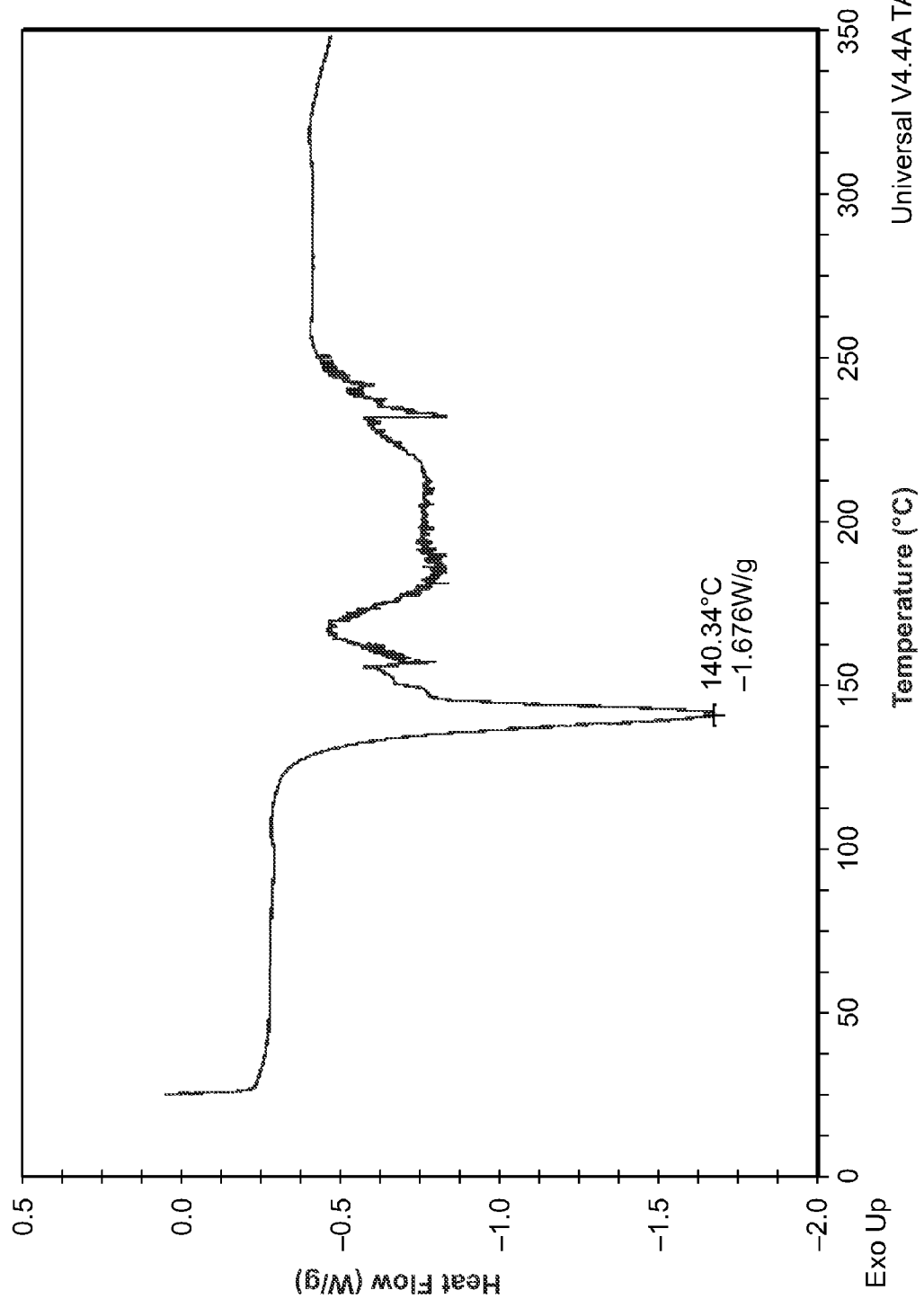
FIG. 9 shows a Differential Scanning calorimetry trace of Formula (I) Mucic Acid Salt—Form B (Example 3).
Figure 12:
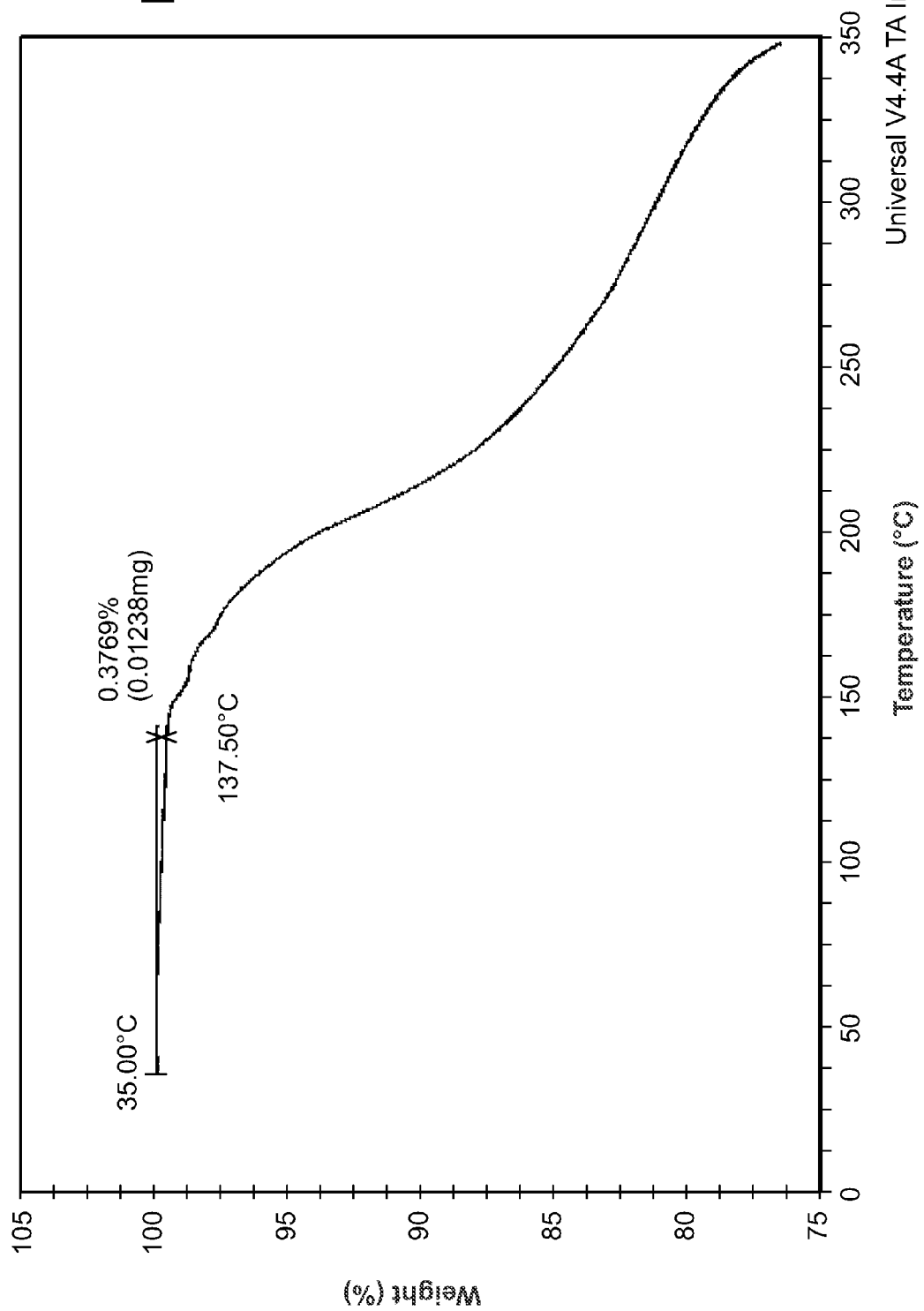
FIG. 12 shows a Thermogravimetric Analysis trace of Formula (I) Mucic Acid Salt—Form B (Example 3)

Another embodiment of the present invention is directed to a crystalline form of Formula (I) Mucic Acid Salt, providing a differential scanning calorimetry trace substantially in accordance with FIG. 9 and/or a thermogravimetric analysis trace substantially in accordance with FIG. 12.

Figure 10:
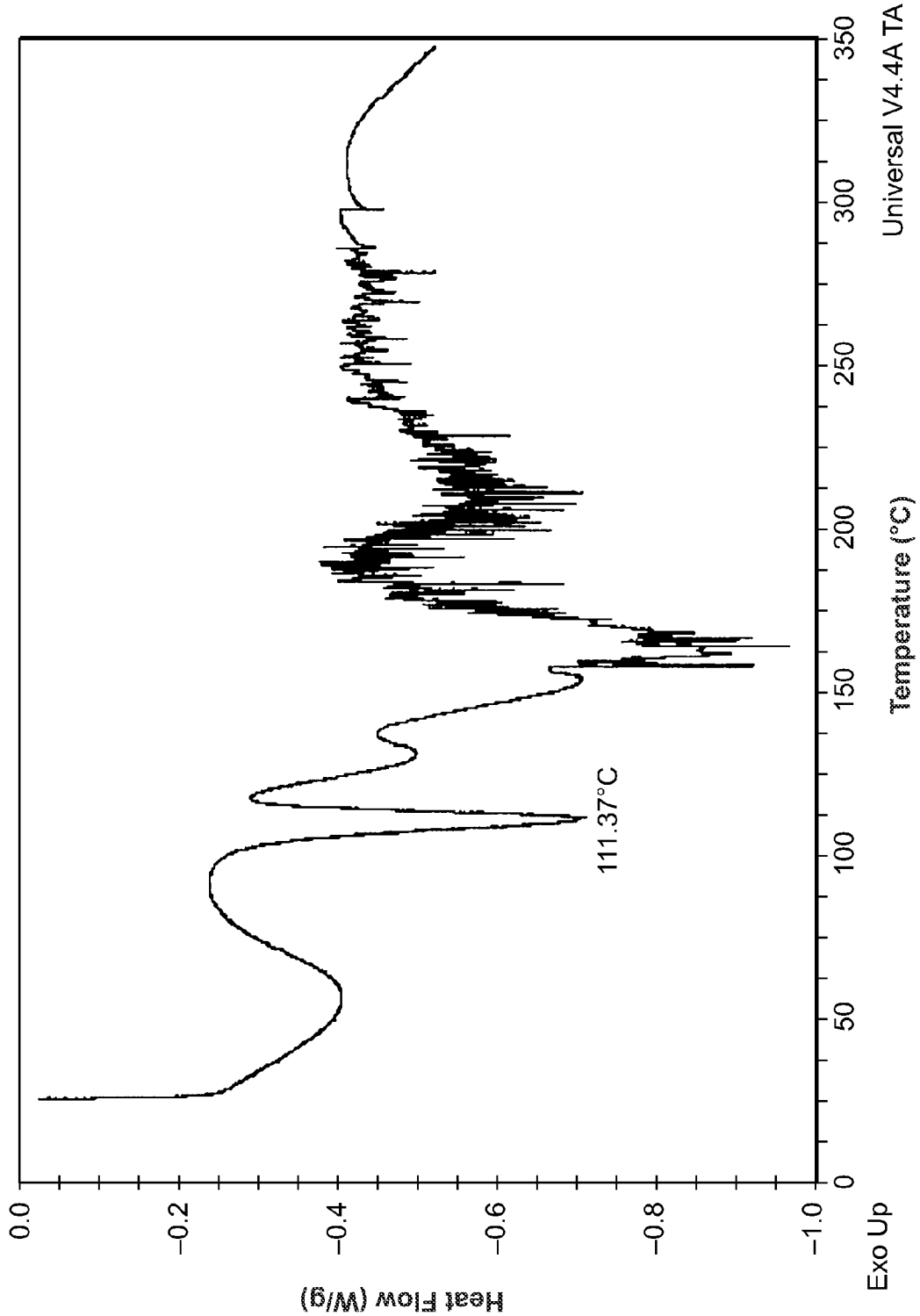
FIG. 10 shows a Differential Scanning calorimetry trace of Formula (I) Mucic Acid Salt—Form C (Example 5).
Figure 13:
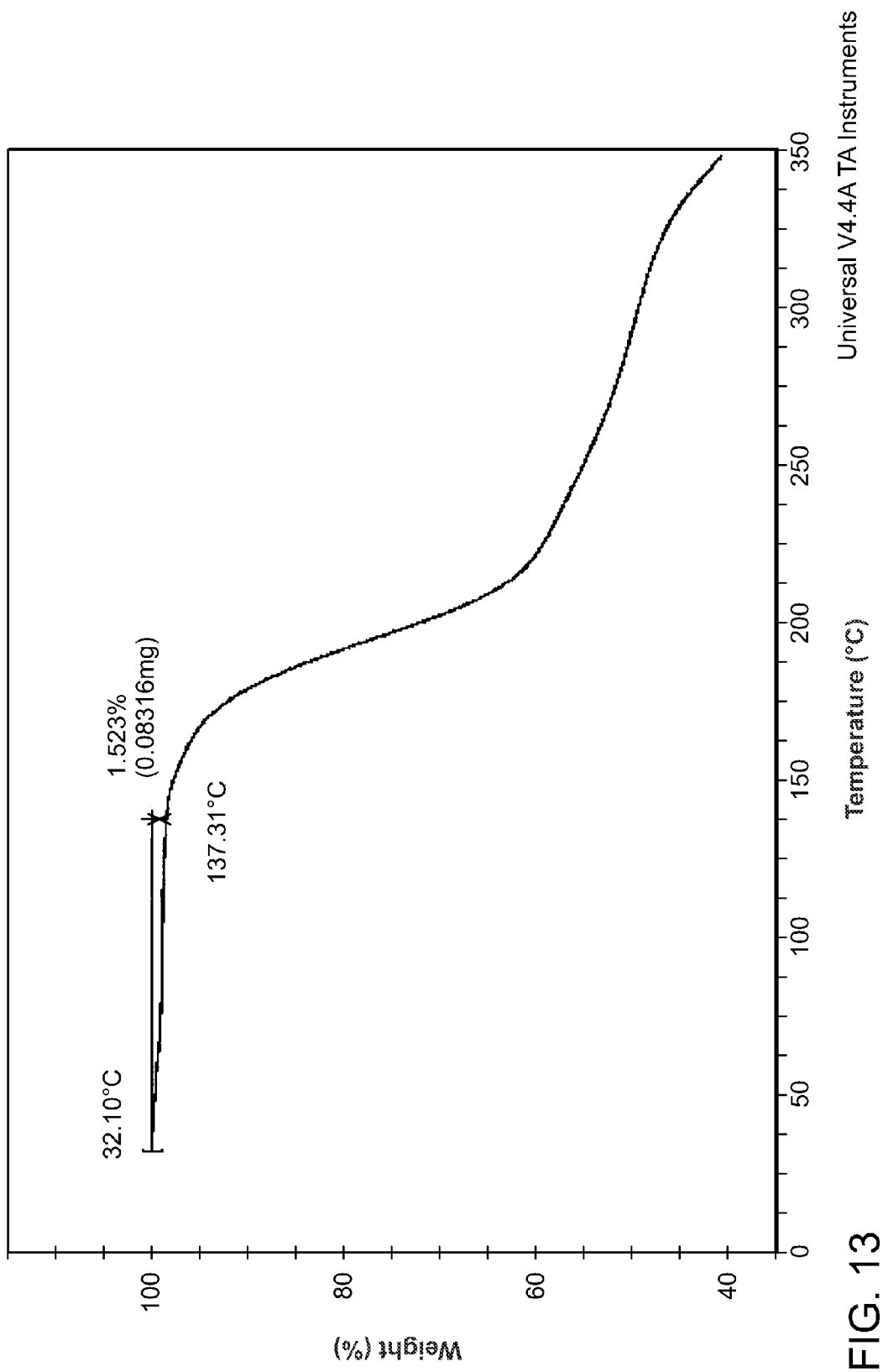
FIG. 13 shows a Thermogravimetric Analysis trace of Formula (I) Mucic Acid Salt—Form C (Example 5)

Another embodiment of the present invention is directed to a crystalline form of Formula (I) Mucic Acid Salt, providing a differential scanning calorimetry trace substantially in accordance with FIG. 10 and/or a thermogravimetric analysis trace substantially in accordance with FIG. 13.

Figure 11:
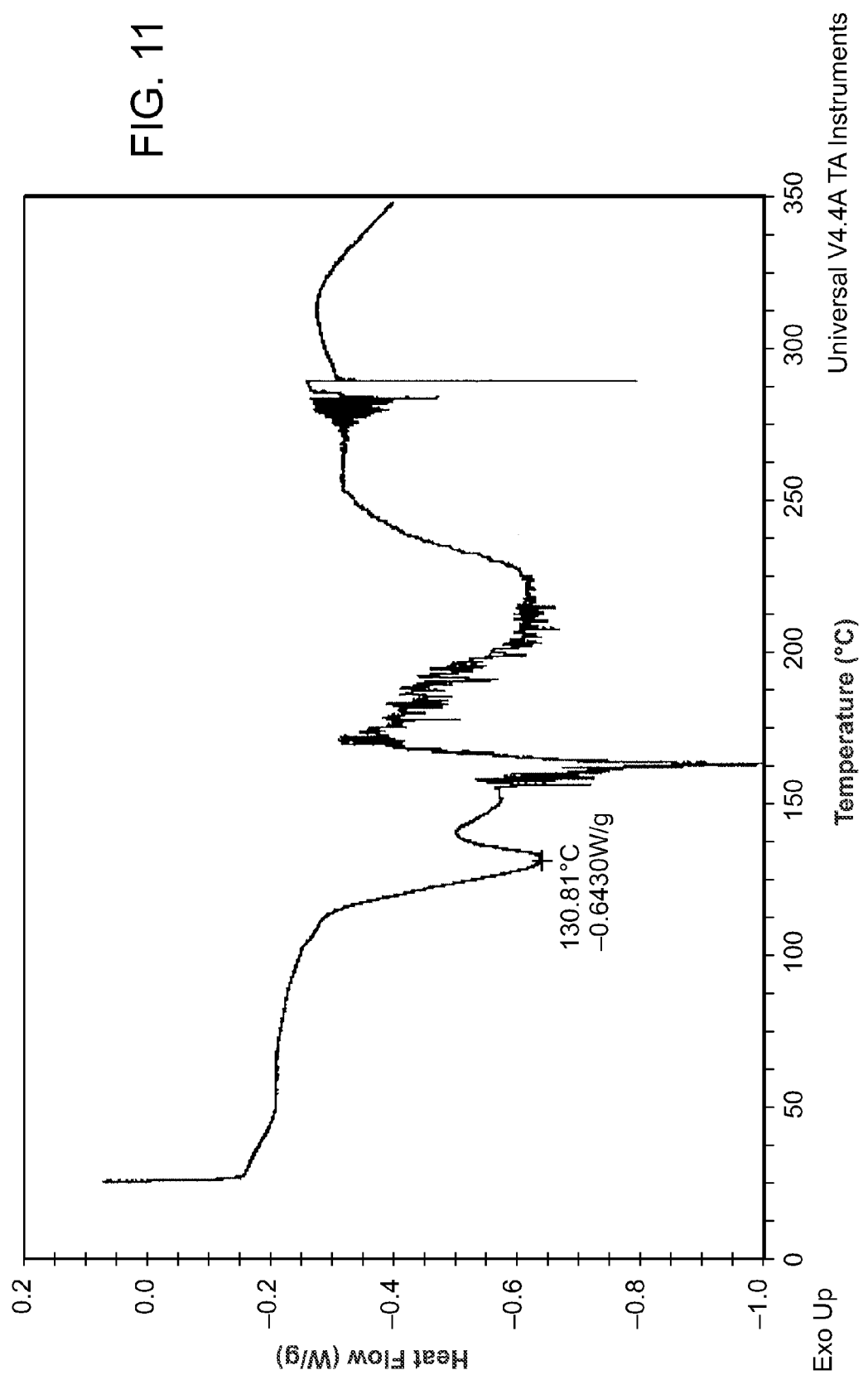
FIG. 11 shows a Differential Scanning calorimetry trace of Formula (I) Mucic Acid Salt—Form D (Example 6).
Figure 14:
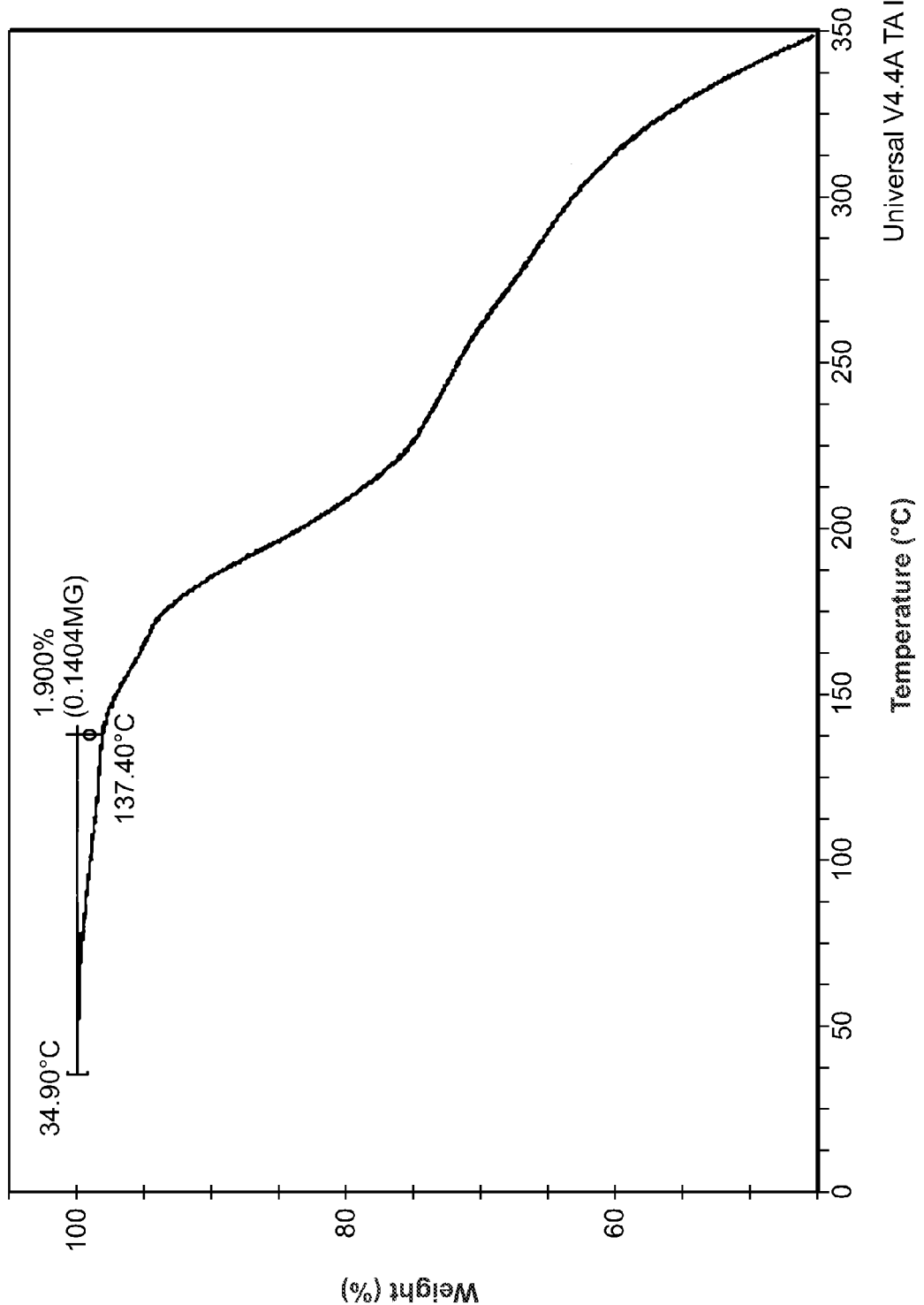
FIG. 14 shows a Thermogravimetric Analysis trace of Formula (I) Mucic Acid Salt—Form D (Example 6)

Another embodiment of the present invention is directed to a crystalline form of Formula (I) Mucic Acid Salt, providing a differential scanning calorimetry trace substantially in accordance with FIG. 11 and/or a thermogravimetric analysis trace substantially in accordance with FIG. 14.

Another embodiment of the present invention is Formula (I) Mucic Acid Salt, wherein the salt is of single crystalline form Form B, Form C, or Form D.

Another embodiment of the present invention is Formula (I) Mucic Acid Salt, wherein the salt comprises one or more of single crystalline forms Form B, Form C and Form D, and optionally amorphous mucic acid salt of Formula (I).

In a particular embodiment the present invention, at least a detectable percentage by weight of Formula (I) Mucic Acid Salt is a single crystalline form of Formula (I) Mucic Acid Salt. A "detectable percentage" refers to a sample with such percentage by weight of the salt of the single crystalline form that allows detection of the single crystalline form using XRPD analysis, for example, as described in Example 7.

A further embodiment of the present invention is a method for preparing a crystalline form of Formula (I) Mucic Acid Salt comprising (a) forming a solution including Formula (I) Free Base and appropriate solvent such as acetonitrile, (b) forming a solution from the solution of (a) with mucic acid and water, (c) lowering the water content of the solution of (b), for example, by azeotropic distillation with an appropriate solvent such as acetonitrile, to form a residue, (d) taking up the residue in an appropriate solvent such as acetonitrile, (e) heating, (f) cooling, (g) filtering, (h) washing with an appropriate solvent, and (i) drying.

Another embodiment is a crystalline form of Formula (I) Mucic Acid Salt prepared by a method comprising (a) forming a solution including Formula (I) Free Base and appropriate solvent such as acetonitrile, (b) forming a solution from the solution of (a) with mucic acid and water, (c) lowering the water content of the solution of (b), for example, by azeotropic distillation with an appropriate solvent such as acetonitrile, to form a residue, (d) taking up the residue in an appropriate solvent such as acetonitrile, (e) heating, (f) cooling, (g) filtering, (h) washing with an appropriate solvent, and (i) drying.

A further embodiment of the present invention is a method for preparing a crystalline form of Formula (I) Mucic Acid Salt comprising (a) refluxing a slurry of mucic acid, appropriate solvent such as acetonitrile and Formula (I) Free Base to form a mixture, (b) filtering the mixture (c) while hot, (e) heating and stirring, (f) cooling, (g) filtering, and (h) removing solvent such as acetonitrile under vacuum.

Another embodiment is a crystalline form of Formula (I) Mucic Acid Salt prepared by a method comprising (a) refluxing a slurry of mucic acid, appropriate solvent such as acetonitrile and Formula (I) Free Base to form a mixture, (b) filtering the mixture (c) while hot, (e) heating and stirring, (f) cooling, (g) filtering, and (h) removing solvent such as acetonitrile under vacuum.

A further embodiment of the present invention is a method for preparing a crystalline form of Formula (I) Mucic Acid Salt comprising (a) heating a slurry of mucic acid, appropriate solvent such as deionized water and Formula (I) Free Base to form a solution, (b) cooling and filtering the solution to form a filtrate, (c) removing solvent from the filtrate to form a residue, using for example a rotary evaporator, (d) taking the residue up in an appropriate solvent such as acetone or methyl ethyl ketone, (e) removing the solvent of (d), (f) taking the residue up in an appropriate solvent such as acetone or methyl ethyl ketone to form a solution, (g) refluxing the solution of (f), (i) cooling, (j) filtering to collect crystals, (k) washing with an appropriate solvent such as ethyl acetate, and (l) drying the crystals, preferably, under vacuum.

Another embodiment is a crystalline form of Formula (I) Mucic Acid Salt prepared by a method comprising (a) heating a slurry of mucic acid, appropriate solvent such as deionized water and Formula (I) Free Base to form a solution, (b) cooling and filtering the solution to form a filtrate, (c) removing solvent from the filtrate to form a residue, using for example a rotary evaporator, (d) taking the residue up in an appropriate solvent such as acetone or methyl ethyl ketone, (e) removing the solvent of (d), (f) taking the residue up in an appropriate solvent such as acetone or methyl ethyl ketone to form a solution, (g) refluxing the solution of (f), (i) cooling, (j) filtering to collect crystals, (k) washing with an appropriate solvent such as ethyl acetate, and (l) drying the crystals, preferably, under vacuum.

As used herein, "crystalline" refers to a solid having a crystal structure wherein the individual molecules have a highly homogeneous regular locked-in chemical configuration. A crystalline form of Formula (I) Mucic Acid Salt can be crystals of a single crystalline form of Formula (I) Mucic Acid Salt, or a mixture of crystals of different single crystalline forms. A single crystalline form means Formula (I) Mucic Acid Salt as a single crystal or a plurality of crystals in which each crystal has the same crystal form.

When a particular percentage by weight of Formula (I) Mucic Acid Salt is a single crystalline form, the remainder of Formula (I) Mucic Acid Salt is provided by one or more other crystalline forms of Formula (I) Mucic Acid Salt excluding the single crystalline form for which the particular percentage by weight is given. Examples of a single crystalline form include Form B of Formula (I) Mucic Acid Salt, Form C of Formula (I) Mucic Acid Salt, and Form D of Formula (I) Mucic Acid Salt, each characterized by one or more properties as discussed herein.

Because mucic acid has two carboxylic acid groups, it can form salts with differing molar ratios of the compound represented by Formula (I) to mucate (the conjugate base of mucic acid). For example, the salt in which there is about a one to one molar ratio of mucate to Formula (I) is Formula (I) Mucate (1 mucate: 1 Formula (I)); and the salt in which there is about a one to two molar ratio of mucate to Formula (I) is Formula (I) Hemi-mucate (1 mucate: 2 Formula (I)).

In some embodiments of the present invention, the Formula (I) Mucic Acid Salts can be solvates, for example, hydrates. The term "solvates" refers to crystalline forms wherein solvent molecules are incorporated into the crystal lattice during crystallization. Solvates may include water or nonaqueous solvents such as ethanol, dimethyl sulfoxide, acetic acid, ethanolamine, acetonitrile, acetone, tetrahydrofuran and ethyl acetate. Solvates, wherein water is the solvent molecule incorporated into the crystal lattice, are typically referred to as "hydrates". Hydrates include stoichiometric hydrates (e.g. a monohydrate), as well as compositions containing variable amounts of water (e.g. a hemi-hydrate).

It is well known and understood to those skilled in the art that the apparatus employed, humidity, temperature, orientation of the powder crystals, and other parameters involved in obtaining an X-ray powder diffraction (XRPD) pattern may cause some variability in the appearance, intensities, and positions of the lines in the diffraction pattern. An X-ray powder diffraction pattern (processed or not processed) that is "substantially in accordance" with one or more figures (showing processed or not processed XRPD patterns, respectively) provided herein is an XRPD pattern that would be considered by one skilled in the art to represent the same single crystalline form of Formula (I) Mucic Acid Salt as the Formula (I) Mucic Acid Salt that provided the XRPD pattern of one or more figures provided herein. For example, the XRDP patterns of FIG. 1 and FIG. 2 provided herein are substantially in accordance, because they both represent Formula (I) Mucic Acid Salts that include the single crystalline form Form B of Formula (I) Mucic Acid Salt, even though they (1) exhibit different backgrounds (without wanting to be bound by theory this is believed to be caused primarily if not entirely by different percentages by weight of amorphous form), (2) exhibit corresponding significant lines/peaks (see Tables 1 and 2 in Example 7) that differ in 2θ angles (for example, the significant peak at 19.28° (see Table 1) as compared to the corresponding significant peak at 19.16° (see Table 2)) and relative intensities (for example, the significant peak at 7.62° with a relative intensity of 66% (see Table 1) as compared to the corresponding significant peak at 7.61° with a relative intensity of 49% (see Table 2)), and (3) contain significant peaks in one XRDP pattern that are not discernible in the other. Thus, an XRPD pattern that is substantially in accordance may be identical to that of one figure, or more likely it may be somewhat different from one or more figures. Such an XRPD pattern may not necessarily show each of the lines of the diffraction patterns presented herein, and/or may show a slight change in appearance, intensity, or a shift in position of said lines resulting from differences in the conditions involved in obtaining the data, or resulting from the presence or difference in percentage by weight of salt of amorphous form. A person skilled in the art is capable of determining if a sample of a crystalline compound has the same form as, or a different form from, a form disclosed herein by comparison of their XRPD patterns. For example, one skilled in the art can overlay an XRPD pattern of a sample of Formula (I) Mucic Acid Salt with FIG. 1 and, using expertise and knowledge in the art, readily determine whether the XRPD pattern of the sample is substantially in accordance with the XRPD pattern of Form B of Formula (I) Mucic Acid Salt. If the XRPD pattern is substantially in accordance with FIG. 1, the sample form can be readily and accurately identified as having the same form as Form B of Formula (I) Mucic Acid Salt. Similarly, a person skilled in the art is capable of determining if a given diffraction angle (expressed in ° 2θ) obtained from an XRPD pattern is at about the same position as a value presented herein. It is to be understood that any 2θ angle specified herein, with the exception of the 2θ angles given in the Example sections or in the Figures, means the specified value±0.2°. For example, if a described embodiment or claim specifies a 2θ angle of 6.57°, this is to be understood to mean 6.57°±0.2°, that is a 2θ angle from 6.37° to 6.77°.

With regard to a differential scanning calorimetry (DSC) trace or thermogravimetric analysis (TGA) trace, "substantially in accordance" with a figure (showing a DSC trace or TGA trace, respectively) provided herein is a DSC trace or TGA trace that would be considered by one skilled in the art to represent the same single crystalline form of Formula (I) Mucic Acid Salt as the Formula (I) Mucic Acid Salt that provided the DCS trace or TGA trace of the figure provided herein.

As used herein, "major x-ray powder diffraction peak" refers to a peak in an x-ray powder diffraction pattern (or, diffractogram) with a relative intensity greater than 40%. Relative intensity is calculated as the ratio of the peak intensity of the peak of interest versus the peak intensity of the largest peak for peaks considered up to 35°. Peak intensities are determined from corresponding peaks in a processed x-ray powder diffraction diagram that is obtained by removing the background intensity (typically, due to intensity contributions of amorphous form of Formula (I) Mucic Acid Salt) from the x-ray powder diffraction pattern.

As used herein a subject is a mammal, preferably a human patient, but can also be an animal in need of veterinary treatment, such as a companion animal (e.g., dogs, cats, and the like), a farm animal (e.g., cows, sheep, pigs, horses, and the like) or a laboratory animal (e.g., rats, mice, guinea pigs, and the like). Subject and patient are used interchangeably.

A subject in need of treatment is a subject with a condition or disease that benefits from antagonizing one or more aspartic proteases.

An "effective amount" refers to an amount effective to inhibit development of, or to alleviate the existing symptoms of the subject being treated with minimal unacceptable side effects. Determination of the effective amount is well within the capability of those skilled in the art, especially in light of the detailed disclosure provided herein. Toxicity and therapeutic efficacy of such compounds can be determined by standard pharmaceutical procedures in cell cultures or experimental animals, e.g., for determining the $LD_{50}$ (the dose lethal to 50% of the population) and $ED_{50}$ (the dose that provides 50% of the maximal response and/or is therapeutically effective in 50% of the population). The dosage can vary within this range depending upon the dosage form employed, and the route of administration utilized. The exact formulation, route of administration, and dosage is chosen by the individual physician in view of the patient's condition. Dosage amount and interval can be adjusted individually to provide plasma levels of the active compound that are sufficient to maintain desired therapeutic effects. In addition to the patient's condition and the mode of administration, the dose administered would depend on the severity of the patient's symptoms and the patient's age and weight. Typically, the pharmaceutical compositions of the invention are administered for a sufficient period of time to achieve the desired therapeutic effect. Dosages may range from 0.01 to 500 mg/kg body weight per day. In one embodiment, the dosing range is 0.1-5.0 mg/kg/day. The compound of the invention may be administered continuously or at specific timed intervals. For example, the compound of the invention may be administered 1, 2, 3, or 4 times per day, such as, e.g., a daily or twice-daily formulation. Commercially available assays may be employed to determine optimal dose ranges and/or schedules for administration.

In one embodiment, the method of the present invention is a mono-therapy where the pharmaceutical compositions of the invention are administered alone. Accordingly, in this embodiment, the Formula (I) Mucic Acid Salt is the only pharmaceutically active ingredient in the pharmaceutical compositions.

In another embodiment, the method of the invention is a co-therapy with other therapeutically active drugs known in the art for treating the desired diseases or indications. The Formula (I) Mucic Acid Salt can be administered before, after or concurrently with one or more other therapeutic agents. In some embodiments, a compound of the invention and other therapeutic agent can be co-administered simultaneously (e.g., concurrently) as either separate formulations or as a joint formulation. Alternatively, the agents can be administered sequentially, as separate compositions, within an appropriate time frame, as determined by the skilled clinician (e.g., a time sufficient to allow an overlap of the pharmaceutical effects of the therapies). A Formula (I) Mucic Acid Salt and one or more other therapeutic agents can be administered in a single dose or in multiple doses, in an order and on a schedule suitable to achieve a desired therapeutic effect.

The Formula (I) Mucic Acid Salt is useful for ameliorating or treating disorders or diseases in which decreasing the levels of aspartic protease products is effective in treating the disease state or in treating infections in which the infectious agent depends upon the activity of an aspartic protease. In hypertension, elevated levels of angiotensin I, the product of renin catalyzed cleavage of angiotensinogen, are present. Thus, the Formula (I) Mucic Acid Salt can be used in the treatment of hypertension; heart failure, such as (acute and chronic) congestive heart failure; left ventricular dysfunction; cardiac hypertrophy; cardiac fibrosis; cardiomyopathy (e.g. diabetic cardiac myopathy and post-infarction cardiac myopathy); supraventricular and ventricular arrhythmias; arial fibrillation; atrial flutter; detrimental vascular remodeling; myocardial infarction and its sequelae; atherosclerosis; angina (whether unstable or stable); renal failure conditions, such as diabetic nephropathy; glomerulonephritis; renal fibrosis; scleroderma; glomerular sclerosis; microvascular complications, for example, diabetic retinopathy; renal vascular hypertension; vasculopathy; neuropathy; complications resulting from diabetes, including nephropathy, vasculopathy, retinopathy and neuropathy; diseases of the coronary vessels; proteinuria; albumenuria; post-surgical hypertension; metabolic syndrome; obesity; restenosis following angioplasty; eye diseases and associated abnormalities including raised intra-ocular pressure, glaucoma, retinopathy, abnormal vascular growth and remodeling; angiogenesis-related disorders, such as neovascular age related macular degeneration; hyperaldosteronism; anxiety states; and cognitive disorders (Fisher N. D.; Hollenberg N. K. *Expert Opin. Investig. Drugs.* 2001, 10, 417-26).

Elevated levels of β-☐amyloid, the product of the activity of the well-characterized aspartic protease β-secretase (BACE) activity on amyloid precursor protein, are widely believed to be responsible for the development and progression of amyloid plaques in the brains of Alzheimer's disease patients. The secreted aspartic proteases of *Candida albicans* are associated with its pathogenic virulence (Naglik, J. R.; Challacombe, S. J.; Hube, B. *Microbiology and Molecular Biology Reviews* 2003, 67, 400-428). The viruses HIV and HTLV depend on their respective aspartic proteases for viral maturation. *Plasmodium falciparum* uses plasmepsins I and II to degrade hemoglobin.

The invention includes a therapeutic method for treating or ameliorating an aspartic protease mediated disorder in a subject in need thereof comprising administering to a subject in need thereof an effective amount of a salt of the invention.

"Aspartic protease mediated disorder or disease" includes disorders or diseases associated with the elevated expression or overexpression of aspartic proteases and conditions that accompany such diseases.

Administration methods include administering an effective amount of a salt or composition of the present invention at different times during the course of therapy or concurrently in a combination form. The methods of the invention include all known therapeutic treatment regimens.

An embodiment of the invention includes administering a Mucic Acid Salt of the invention in a combination therapy (see U.S. Pat. No. 5,821,232, U.S. Pat. No. 6,716,875, U.S. Pat. No. 5,663,188, Fossa, A. A.; DePasquale, M. J.; Ringer, L. J.; Winslow, R. L. "Synergistic effect on reduction in blood pressure with coadministration of a renin inhibitor or an angiotensin-converting enzyme inhibitor with an angiotensin II receptor antagonist" *Drug Development Research* 1994, 33(4), 422-8, the aforementioned article and patents are hereby incorporated by reference) with one or more additional agents for the treatment of hypertension including α-blockers, β-blockers, calcium channel blockers, diuretics, natriuretics, saluretics, centrally acting antihypertensives, angiotensin converting enzyme (ACE) inhibitors, dual ACE and neutral endopeptidase (NEP) inhibitors, angiotensin-receptor blockers (ARBs), aldosterone synthase inhibitor, aldosterone-receptor antagonists, or endothelin receptor antagonist.

α-Blockers include doxazosin, prazosin, tamsulosin, and terazosin.

β-Blockers for combination therapy are selected from atenolol, bisoprol, metoprolol, acetutolol, esmolol, celiprolol, taliprolol, acebutolol, oxprenolol, pindolol, propanolol, bupranolol, penbutolol, mepindolol, carteolol, nadolol, carvedilol, and their pharmaceutically acceptable salts.

Calcium channel blockers include dihydropyridines (DHPs) and non-DHPs. The preferred DHPs are selected from the group consisting of amlodipine, felodipine, ryosidine, isradipine, lacidipine, nicardipine, nifedipine, nigulpidine, niludipine, nimodiphine, nisoldipine, nitrendipine, and nivaldipine and their pharmaceutically acceptable salts. Non-DHPs are selected from flunarizine, prenylamine, diltiazem, fendiline, gallopamil, mibefradil, anipamil, tiapamil, and verampimil and their pharmaceutically acceptable salts.

A diuretic is, for example, a thiazide derivative selected from amiloride, chlorothiazide, hydrochlorothiazide, methylchlorothiazide, and chlorothalidon.

Centrally acting antihypertensives include clonidine, guanabenz, guanfacine and methyldopa.

ACE inhibitors include alacepril, benazepril, benazaprilat, captopril, ceronapril, cilazapril, delapril, enalapril, enalaprilat, fosinopril, lisinopril, moexipiril, moveltopril, perindopril, quinapril, quinaprilat, ramipril, ramiprilat, spirapril, temocapril, trandolapril, and zofenopril. Preferred ACE inhibitors are benazepril, enalpril, lisinopril, and ramipril.

Dual ACE/NEP inhibitors are, for example, omapatrilat, fasidotril, and fasidotrilat.

Preferred ARBs include candesartan, eprosartan, irbesartan, losartan, olmesartan, tasosartan, telmisartan, and valsartan.

Preferred aldosterone synthase inhibitors are anastrozole, fadrozole, and exemestane.

Preferred aldosterone-receptor antagonists are spironolactone and eplerenone.

A preferred endothelin antagonist is, for example, bosentan, enrasentan, atrasentan, darusentan, sitaxentan, and tezosentan and their pharmaceutically acceptable salts.

An embodiment of the invention includes administering a Formula (I) Mucic Acid Salt of the invention or a pharmaceutical composition containing the same in a combination therapy with one or more additional agents for the treatment of AIDS reverse transcriptase inhibitors, non-nucleoside reverse transcriptase inhibitors, other HIV protease inhibitors, HIV integrase inhibitors, entry inhibitors (including attachment, co-receptor and fusion inhibitors), antisense drugs, and immune stimulators.

Preferred reverse transcriptase inhibitors are zidovudine, didanosine, zalcitabine, stavudine, lamivudine, abacavir, tenofovir, and emtricitabine.

Preferred non-nucleoside reverse transcriptase inhibitors are nevirapine, delaviridine, and efavirenz.

Preferred HIV protease inhibitors are saquinavir, ritonavir, indinavir, nelfinavir, amprenavir, lopinavir, atazanavir, and fosamprenavir.

Preferred HIV integrase inhibitors are L-870, 810 and S-1360.

Entry inhibitors include compounds that bind to the CD4 receptor, the CCR5 receptor or the CXCR4 receptor. Specific examples of entry inhibitors include enfuvirtide (a peptidomimetic of the HR2 domain in gp41) and sifurvitide.

A preferred attachment and fusion inhibitor is enfuvirtide.

An embodiment of the invention includes administering a Formula (I) Mucic Acid Salt of the invention or a pharmaceutical composition containing the same in a combination therapy with one or more additional agents for the treatment of Alzheimer's disease including tacrine, donepezil, rivastigmine, galantamine, and memantine.

An embodiment of the invention includes administering a Formula (I) Mucic Acid Salt of the invention or a pharmaceutical composition containing the same in a combination therapy with one or more additional agents for the treatment of malaria including artemisinin, chloroquine, halofantrine, hydroxychloroquine, mefloquine, primaquine, pyrimethamine, quinine, sulfadoxine.

Combination therapy includes co-administration of a Formula (I) Mucic Acid Salt of the invention and said other agent, sequential administration of the Formula (I) Mucic Acid Salt of the invention and the other agent, administration of a composition containing the Formula (I) Mucic Acid Salt of the invention and the other agent, or simultaneous administration of separate compositions containing the Formula (I) Mucic Acid Salt of the invention and the other agent.

The Formula (I) Mucic Acid Salts of the invention may also be administered via a delayed release composition, wherein the composition includes a Formula (I) Mucic Acid Salt of the invention and a biodegradable slow release carrier (e.g. a polymeric carrier) or a pharmaceutically acceptable non-biodegradable slow release carrier (e.g. an ion exchange carrier).

Biodegradable and non-biodegradable delayed release carriers are well known in the art. Biodegradable carriers are used to form particles or matrices which retain a drug substance(s) (i.e. Formula (I) Mucic Acid Salts of the present invention) and which slowly degrade/dissolve in a suitable environment (e.g. aqueous, acidic, basic and the like) to release the drug substance(s). Such particles degrade/dissolve in body fluids to release the drug substance(s) (i.e. Formula (I) Mucic Acid Salts of the present invention) therein. The particles are preferably nanoparticles (e.g. in the range of about 1 to 500 nm in diameter, preferably about 50-200 nm in diameter, and most preferably about 100 nm in diameter). In a process for preparing a slow release composition, a slow release carrier and a Formula (I) Mucic Acid Salt of the invention are first dissolved or dispersed in an organic solvent. The resulting mixture is added into an aqueous solution containing an optional surface-active agent(s) to produce an emulsion. The organic solvent is then evaporated from the emulsion to provide a colloidal suspension of particles containing the slow release carrier and the Formula (I) Mucic Acid Salt of the invention.

The Formula (I) Mucic Acid Salts of the invention may be incorporated for administration orally or by injection in a liquid form, such as aqueous solutions, suitably flavored syrups, aqueous or oil suspensions, flavored emulsions with edible oils such as cottonseed oil, sesame oil, coconut oil or peanut oil and the like, or in elixirs or similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone, and gelatin. The liquid forms in suitably flavored suspending or dispersing agents may also include synthetic and natural gums. For parenteral administration, sterile suspensions and solutions are desired. Isotonic preparations, which generally contain suitable preservatives, are employed when intravenous administration is desired.

The Formula (I) Mucic Acid Salts of the invention may be administered parenterally via injection. A parenteral formulation may consist of the drug substance (i.e. Formula (I) Mucic Acid Salts of the present invention) dissolved in or mixed with an appropriate inert liquid carrier. Acceptable liquid carriers usually comprise aqueous solvents and other optional ingredients for aiding solubility or preservation. Such aqueous solvents include sterile water, Ringer's solution, or an isotonic aqueous saline solution. Other optional ingredients include vegetable oils (such as peanut oil, cottonseed oil, and sesame oil), and organic solvents (such as solketal, glycerol, and formyl). A sterile, non-volatile oil may be employed as a solvent or suspending agent. The parenteral formulation is prepared by dissolving or suspending the drug substance (i.e. Formula (I) Mucic Acid Salts of the present invention) in the liquid carrier whereby the final dosage unit contains from 0.005 to 10% by weight of the drug substance (i.e. Formula (I) Mucic Acid Salts of the present invention). Other additives include preservatives, isotonizers, solubilizers, stabilizers, and pain-soothing agents. Injectable suspensions may also be prepared, in which case appropriate liquid carriers, suspending agents and the like may be employed.

The Formula (I) Mucic Acid Salts of the invention may be administered intranasally using a suitable intranasal vehicle.

The Formula (I) Mucic Acid Salts of the invention may also be administered topically using a suitable topical transdermal vehicle or a transdermal patch.

For ocular administration, a pharmaceutical composition containing a Formula (I) Mucic Acid Salt of the invention is preferably in the form of an ophthalmic composition. The ophthalmic compositions are preferably formulated as eye-drop formulations and filled in appropriate containers to facilitate administration to the eye, for example a dropper fitted with a suitable pipette. Preferably, the compositions are sterile and aqueous based, using purified water. In addition to the Formula (I) Mucic Acid Salt of the invention, an ophthalmic composition may contain one or more of: a) a surfactant such as a polyoxyethylene fatty acid ester; b) a thickening agents such as cellulose, cellulose derivatives, carboxyvinyl polymers, polyvinyl polymers, and polyvinylpyrrolidones, typically at a concentration n the range of about 0.05 to about 5.0% (wt/vol); c) (as an alternative to or in addition to storing the composition in a container containing nitrogen and optionally including a free oxygen absorber such as Fe), an anti-oxidant such as butylated hydroxyanisol, ascorbic acid, sodium thiosulfate, or butylated hydroxytoluene at a concentration of about 0.00005 to about 0.1% (wt/vol); d) ethanol at a concentration of about 0.01 to 0.5% (wt/vol); and e) other excipients such as an isotonic agent, buffer, preservative, and/or pH-controlling agent. The pH of the ophthalmic composition is desirably within the range of 4 to 8.

The invention includes the use of Formula (I) Mucic Acid Salts of the invention for the preparation of a composition for treating or ameliorating an aspartic protease mediated chronic disorder or disease or infection in a subject in need thereof, wherein the composition comprises a mixture of one or more of the Formula (I) Mucic Acid Salts of the invention and an optional pharmaceutically acceptable carrier.

The invention further includes the use of Formula (I) Mucic Acid Salts of the invention as an active therapeutic substance, in particular in the treatment of aspartic protease mediated disorders. In particular, the invention includes the use of Formula (I) Mucic Acid Salts of the invention in the treatment of hypertension, congestive heart failure, cardiac hypertrophy, cardiac fibrosis, cardiomyopathy post-infarction, nephropathy, vasculopathy and neuropathy, a disease of the coronary vessels, post-surgical hypertension, restenosis following angioplasty, raised intra-ocular pressure, glaucoma, abnormal vascular growth, hyperaldosteronism, an anxiety state, or a cognitive disorder.

In another aspect, the invention includes the use of Formula (I) Mucic Acid Salts of the invention in the manufacture of a medicament for use in the treatment of the above disorders.

"Pharmaceutically acceptable carrier" means any one or more compounds and/or compositions that are of sufficient purity and quality for use in the formulation of a Formula (I) Mucic Acid Salt of the invention that, when appropriately administered to a human, do not produce an adverse reaction, and that are used as a vehicle for a drug substance (i.e. Formula (I) Mucic Acid Salts of the present invention).

The invention further includes the process for making the composition comprising mixing one or more of the Formula (I) Mucic Acid Salts of the invention and an optional pharmaceutically acceptable carrier; and includes those compositions resulting from such a process, which process includes conventional pharmaceutical techniques. For example, a Formula (I) Mucic Acid Salt of the invention may be nanomilled prior to formulation. A Formula (I) Mucic Acid Salt of the invention may also be prepared by grinding, micronizing or other particle size reduction methods known in the art. Such methods include, but are not limited to, those described in U.S. Pat. Nos. 4,826,689, 5,145,684, 5,298,262, 5,302,401, 5,336,507, 5,340,564, 5,346,702, 5,352,459, 5,354,560, 5,384,124, 5,429,824, 5,503,723, 5,510,118, 5,518,187, 5,518,738, 5,534,270, 5,536,508, 5,552,160, 5,560,931, 5,560,932, 5,565,188, 5,569,448, 5,571,536, 5,573,783, 5,580,579, 5,585,108, 5,587,143, 5,591,456, 5,622,938, 5,662,883, 5,665,331, 5,718,919, 5,747,001, PCT applications WO 93/25190, WO 96/24336, and WO 98/35666, each of which is incorporated herein by reference. The pharmaceutical compositions of the invention may be prepared using techniques and methods known to those skilled in the art. Some of the methods commonly used in the art are described in *Remington's Pharmaceutical Sciences* (Mack Publishing Company), the entire teachings of which are incorporated herein by reference.

The compositions of the invention include ocular, oral, nasal, transdermal, topical with or without occlusion, intravenous (both bolus and infusion), and injection (intraperitoneally, subcutaneously, intramuscularly, intratumorally, or parenterally). The composition may be in a dosage unit such as a tablet, pill, capsule, powder, granule, liposome, ion exchange resin, sterile ocular solution, or ocular delivery device (such as a contact lens and the like facilitating immediate release, timed release, or sustained release), parenteral solution or suspension, metered aerosol or liquid spray, drop, ampoule, auto-injector device, or suppository; for administration ocularly, orally, intranasally, sublingually, parenterally, or rectally, or by inhalation or insufflation.

Compositions of the invention suitable for oral administration include solid forms such as pills, tablets, caplets, capsules (each including immediate release, timed release, and sustained release formulations), granules and powders; and, liquid forms such as solutions, syrups, elixirs, emulsions, and suspensions. Forms useful for ocular administration include sterile solutions or ocular delivery devices. Forms useful for parenteral administration include sterile solutions, emulsions, and suspensions.

The dosage form containing the composition of the invention contains an effective amount of the drug substance (i.e. Formula (I) Mucic Acid Salts of the present invention) necessary to provide a therapeutic and/or prophylactic effect. The composition may contain from about 5,000 mg to about 0.5 mg (preferably, from about 1,000 mg to about 0.5 mg) of a Formula (I) Mucic Acid Salt of the invention and may be constituted into any form suitable for the selected mode of administration. The compositions of the invention may be administered in a form suitable for once-weekly or once-monthly administration. Daily administration or post-periodic dosing may also be employed, wherein the composition may be administered about 1 to about 5 times per day.

For oral administration, the composition is preferably in the form of a tablet or capsule containing, e.g. 1000 to 0.5 milligrams of the drug substance (i.e. Formula (I) Mucic Acid Salts of the present invention), more specifically 500 mg to 5 mg. Dosages will vary depending on factors associated with the particular patient being treated (e.g. age, weight, diet, and time of administration), the severity of the condition being treated, the compound being employed, the mode of administration, and the strength of the preparation.

The oral composition is preferably formulated as a homogeneous composition, wherein the drug substance (i.e. a Formula (I) Mucic Acid Salt of the present invention) is dispersed evenly throughout the mixture, which may be readily subdivided into dosage units containing equal amounts of a Formula (I) Mucic Acid Salt of the invention. Preferably, the compositions are prepared by mixing a Formula (I) Mucic Acid Salt of the invention with one or more optionally present pharmaceutical carriers (such as a starch, sugar, diluent, granulating agent, lubricant, glidant, binding agent, and disintegrating agent), one or more optionally present inert pharmaceutical excipients (such as water, glycols, oils, alcohols, flavoring agents, preservatives, coloring agents, and syrup), one or more optionally present conventional tableting ingredients (such as corn starch, lactose, sucrose, sorbitol, talc, stearic acid, magnesium stearate, dicalcium phosphate, and any of a variety of gums), and an optional diluent (such as water).

Binding agents include starch, gelatin, natural sugars (e.g. glucose and beta-lactose), corn sweeteners and natural and synthetic gums (e.g. acacia and tragacanth). Disintegrating agents include starch, methyl cellulose, agar, and bentonite.

Tablets and capsules represent an advantageous oral dosage unit form. Tablets may be sugarcoated or filmcoated using standard techniques. Tablets may also be coated or otherwise compounded to provide a prolonged, control-release therapeutic effect. The dosage form may comprise an inner dosage and an outer dosage component, wherein the outer component is in the form of an envelope over the inner component. The two components may further be separated by a layer which resists disintegration in the stomach (such as an enteric layer) and permits the inner component to pass intact into the duodenum or a layer which delays or sustains release. A variety of enteric and non-enteric layer or coating materials (such as polymeric acids, shellacs, acetyl alcohol, and cellulose acetate or combinations thereof) may be used.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXPERIMENTAL

Example 1

Preparation of methyl 2-((R)-(3-chlorophenyl)((R)-1-(S)-2-(methylamino)-3-((R)-tetrahydro-2H-pyran-3-yl)propylcarbamoyl)piperidin-3-yl)methoxy)ethylcarbamate from its TFA salt

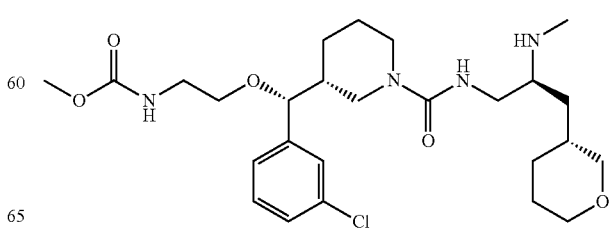

A solution of the trifluoroacetic acid salt of methyl {2-[((R)-(3-chlorophenyl){(3R)-1-[({(2S)-2-(methyl-amino)-3-[(3R)-tetrahydro-2H-pyran-3-yl]propyl}amino)carbonyl]-3-piperidinyl}methyl)oxy]ethyl}carbamate (prepared as in WO 2008/036247) (10.0 g, 15.65 mmol) in 200 mL of dichloromethane was washed successively with 1 N aqueous sodium hydroxide, water, and brine. The organic portion was dried over $Na_2SO_4$ and concentrated in vacuo to afford the title compound as an off-white foam (7.50 g, 91%). $^1$H NMR ($CD_3OD$, 400 MHz) δ ppm 7.38-7.31 (m, 3H), 7.24 (m, 1H), 4.23 (dd, J=13.1, 3.6 Hz, 1H), 4.03 (d, J=8.8 Hz, 1H), 3.84 (m, 3H), 3.64 (s, 3H), 3.42 (ddd, $J_a$=5.8 Hz, $J_b$=7.8 Hz, $J_c$=11.1 Hz, 1H), 3.24-3.30 (m, 5H), 3.16 (dd, $J_a$=6.3 Hz, $J_b$=13.9 Hz, 1H), 3.10 (dd, $J_a$=10 Hz, $J_b$=11 Hz, 1H), 2.88 (m, 2H), 2.66 (m, 1H), 2.42 (s, 3H), 1.97 (m, 1H), 1.75 (m, 2H), 1.65-1.61 (m, 3H), 1.40-1.09 (m, 6H); MS (m/z) 525.3 (M+H$^+$).

Example 2

Preparation of methyl 2-((R)-(3-chlorophenyl)((R)-1-((S)-2-(methylamino)-3-((R)-tetrahydro-2H-pyran-3-yl)propyl carbamoyl)piperidin-3-yl)methoxy)ethylcarbamate HCl salt

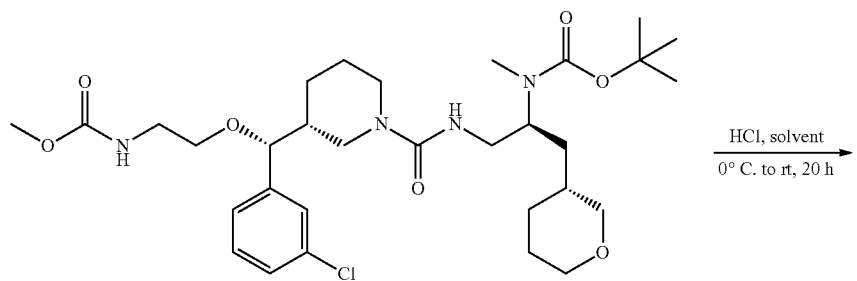

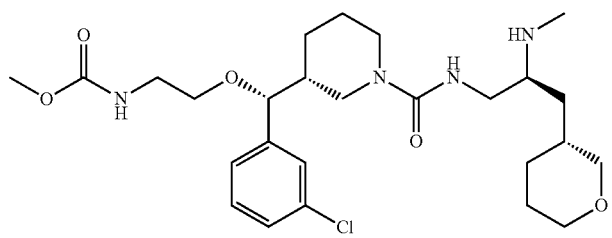

6.15 Kg of methyl 2-((R)-(3-chlorophenyl)((R)-1-(S)-2-(N-t-butoxycarbonyl-N-methylamino)-3-((R)-tetrahydro-2H-pyran-3-yl)propylcarbamoyl)piperidin-3-yl)methoxy)ethylcarbamate was dissolved in 33 L of 1,4-dioxane and the mixture cooled to 11° C. To this solution was added 14 L of 4.0 M HCl in dioxane over a 23 minute period. The mixture was allowed to warm to 20° C. and stir at this temperature for 9 h. After this time HPLC analysis showed 99% conversion to the deprotected amine product. The volatile materials were removed in vacuo to yield the HCl salt of methyl 2-((R)-(3-chlorophenyl)((R)-1-((S)-2-(methylamino)-3-((R)-tetrahydro-2H-pyran-3-yl)propylcarbamoyl)piperidin-3-yl)methoxy)ethylcarbamate as a sticky tar. $^1$H NMR analysis showed that this material (6.86 Kg) contained ~0.2 equiv of dioxane.

Example 3

Preparation of methyl 2-((R)-(3-chlorophenyl)((R)-1-((S)-2-(methylamino)-3-((R)-tetrahydro-2H-pyran-3-yl)propyl carbamoyl)piperidin-3-yl)methoxy)ethylcarbamate mucic acid salt (Form B)

dried over sodium sulfate and the solvent was removed. The residue was taken up in water and mucic acid (105 mg, 0.500 mmol, 0.5 equiv) was added. The mixture was stirred at 45° C. for 30 min. and a clear solution was obtained. The solution was cooled to ambient temperature and filtered through a piece of Whatman-filter paper. The water was removed by azeotropic distillation with acetonitrile (3×5 mL acetonitrile, temperature water bath 70° C., pressure down to 60 mbar). The residue was taken up in acetonitrile (4.5 mL) and warmed to 80° C. whereupon the product precipitated. After 30 min the oil bath was set to 35° C. and the reaction mixture was stirred at this temperature for 1 h. The mixture was allowed to cool to RT and was stored overnight. The product was collected by filtration. The flask was rinsed with acetonitrile (3 mL) and the product was dried on the filter for 45 min. This afforded 454 mg (72% yield) of the Formula (I) hemi-mucate. This product was shown by XRPD to have Form B with some amorphous content (see FIG. 1).

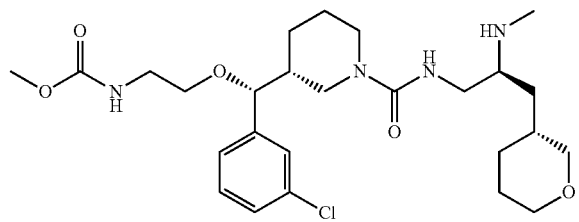 [SMILES: CN[C@H](CNC(=O)N1CCC[C@@H]([C@@H](OCCNC(=O)OC)c2cccc(Cl)c2)C1)C[C@H]1CCCOC1]

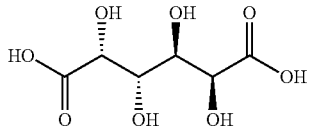

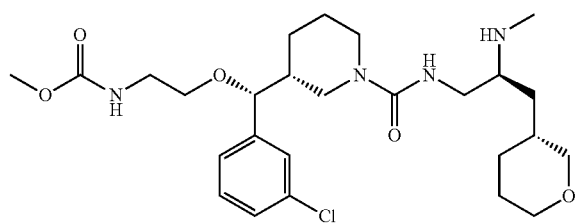

562 mg (1.0 mmol) of methyl 2-((R)-(3-chlorophenyl)((R)-1-((S)-2-(methylamino)-3-((R)-tetrahydro-2H-pyran-3-yl)propylcarbamoyl)piperidin-3-yl)methoxy)ethylcarbamate hydrochloride, prepared as described in Example 2, was taken up in 10 mL ethyl acetate. The mixture was extracted twice with 2 N aq NaOH. The organic layer was

Example 4

Preparation of methyl 2-((R)-(3-chlorophenyl)((R)-1-((S)-2-(methylamino)-3-((R)-tetrahydro-2H-pyran-3-yl)propyl carbamoyl)piperidin-3-yl)methoxy)ethylcarbamate mucic acid salt (Form B)

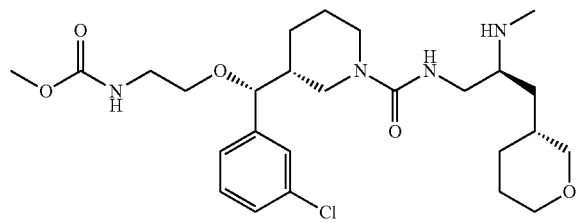

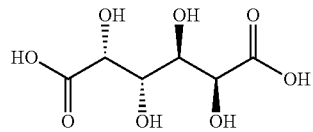

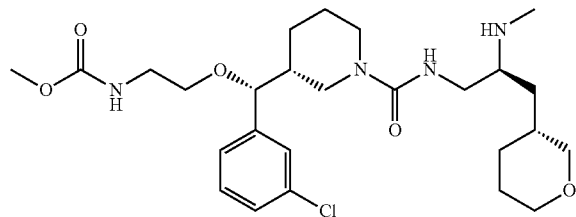

The HCl-salt of methyl 2-((R)-(3-chlorophenyl)((R)-1-(S)-2-(methylamino)-3-((R)-tetrahydro-2H-pyran-3-yl)propylcarbamoyl)piperidin-3-yl)methoxy)ethylcarbamate (5.35 Kg), prepared as described in Example 2, was converted to the free base by treatment of an EtOAc solution with saturated aqueous $NaHCO_3$. The EtOAc solution was concentrated and the residue was redissolved 42 L of acetonitrile and transferred to an addition funnel. In a separate reactor mucic acid (1 Kg) was suspended in 66 L of water. The acetonitrile solution of Formula (I) free base was added to the white suspension. The reactor was warmed to 40° C. to form a solution. After 50 min. most of the solids had dissolved and the contents were transferred to a barrel. The reactor was cleaned and rinsed with acetonitrile. The contents of the barrel were transferred via an inline filter into the reactor. The water content was lowered to <2% by azeotropic distillation with acetonitrile. The residue was taken up in 25 L of acetonitrile and the mixture heated to reflux (jacket temperature 90° C.) to give a clear solution. The mixture was cooled to 20° C. over a 5 h period, then to 3.5° C. over a 3 h period. A thick suspension was produced. This was isolated by filtration on 50 L Nutsch with Teflon filter cloth. The mother liquor was used to rinse the crystals from the reactor. Residual solvent was removed in vacuo till the level of residual acetonitrile was less than 0.01%. This afforded 3.4 Kg of Formula (I) hemi mucate of Form B. The corresponding XRPD pattern is shown in FIG. 2. The melting point of the product was 132-136° C.

Example 5

Preparation of 2:1 methyl 2-((R)-(3-chlorophenyl)((R)-1-(S)-2-(methylamino)-3-((R)-tetrahydro-2H-pyran-3-yl)propylcarbamoyl)piperidin-3-yl)methoxy)ethylcarbamate/mucic acid salt (Form C)

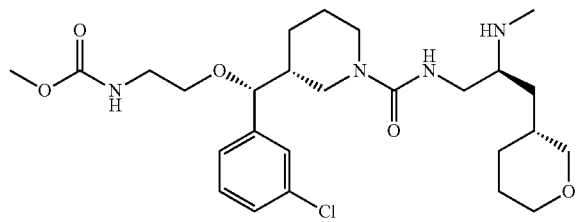

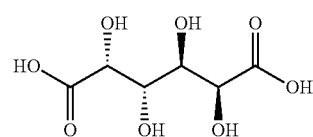

-continued

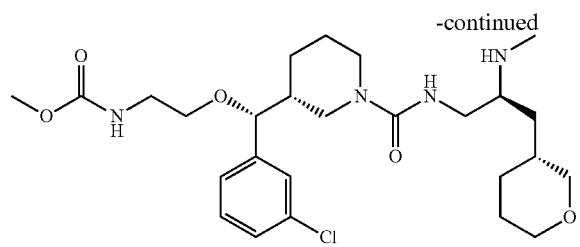

A 100 ml, round-bottom flask, equipped with a ¾×⅜" egg-shaped stir bar and reflux condenser with nitrogen inlet, was charged with 353 mg (1.68 mmol) of mucic acid (Aldrich, as received) and 30 mL of CH₃CN (Aldrich, HPLC grade, anhydrous) and the resulting slurry heated to reflux with a stir rate of 374 rpm (bath temperature=83° C.). In a separate flask a solution of methyl 2-((R)-(3-chlorophenyl)((R)-1-((S)-2-(methylamino)-3-((R)-tetrahydro-2H-pyran-3-yl)propylcarbamoyl)piperidin-3-yl)methoxy)ethylcarbamate (prepared as described in Example 1) was prepared in 7 mL of acetonitrile (same source) and the solution was added to the refluxing slurry of mucic acid. The flask containing the methyl 2-((R)-(3-chlorophenyl)((R)-1-((S)-2-(methylamino)-3-((R)-tetrahydro-2H-pyran-3-yl)propylcarbamoyl)piperidin-3-yl)methoxy)ethylcarbamate was rinsed with 3 mL of acetonitrile and this rinse was added to the reaction flask. The mixture was heated to reflux for 2 h, during which time most of the mucic acid dissolved. While the solution was hot it was quickly filtered through a syringe equipped with a Chromafil O-20/15 MS PTFE filter into a clean 100 mL flask flask was rinsed with ~10 mL of acetonitrile (same source) and the filtered solid lightly agitated with a spatula. ¹H NMR of these solids (1121 mg, 53% yield) was consistent with a 2:1 methyl 2-((R)-(3-chlorophenyl)((R)-1-((S)-2-(methylamino)-3-((R)-tetrahydro-2H-pyran-3-yl)propylcarbamoyl)piperidin-3-yl)methoxy)ethylcarbamate/mucic acid salt which contained ~⅓ equiv of acetonitrile. It has been found experimentally that the acetonitrile can be removed by heating at 45° C. under vacuum or by prolonged (>24 h) exposure to vacuum at ambient temperature. The XRPD pattern for the obtained Formula (I) hemi mucate (Form C) product is shown in FIG. 3.

Example 6

Preparation of 2:1 methyl 2-((R)-(3-chlorophenyl)((R)-1-((S)-2-(methylamino)-3-((R)-tetrahydro-2H-pyran-3-yl)propylcarbamoyl)piperidin-3-yl)methoxy)ethylcarbamate/mucic acid salt (Form D)

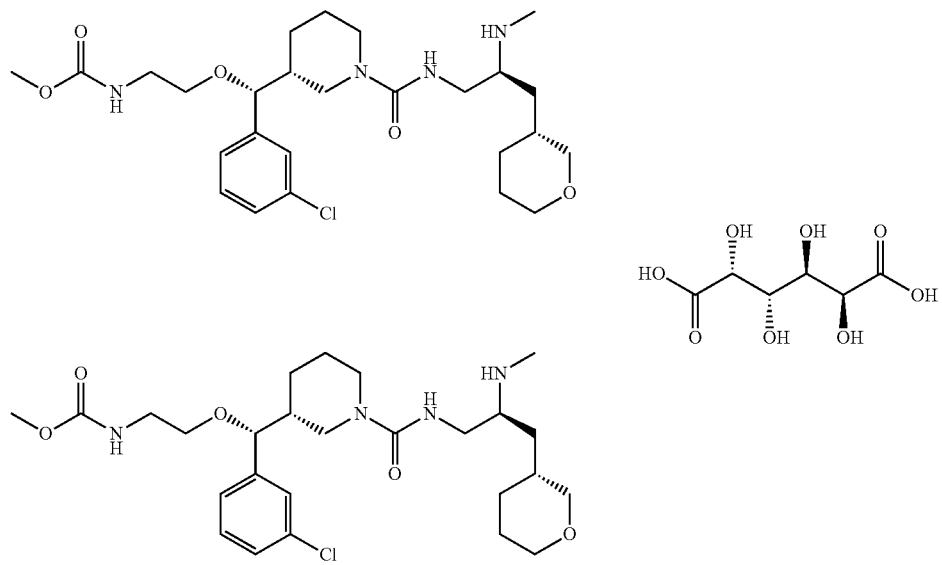

with the same equipment as described above. The resulting clear, colorless solution was heated in an oil bath to 80° C. with a stir rate of 635 rpm. After 30 min the heating source to the oil bath was switched off and the mixture cooled to ambient temperature. After 30 min the bath temperature was 47° C. and some wispy solids were observed in the reaction flask. The mixture was allowed to reach 22° C. and stand overnight. After this time a large amount of white solid was observed. The solids were collected on a piece of Whatman No. 1 filter paper contained in a porcelain crucible filter. The reaction A 50 mL flask was charged with 105 mg (0.50 mmol, 0.5 equiv) of mucic acid, 524 mg (1.0 mmol, 1.0 equiv) of methyl 2-((R)-(3-chlorophenyl)((R)-1-((S)-2-(methylamino)-3-((R)-tetrahydro-2H-pyran-3-yl)propylcarbamoyl)piperidin-3-yl)methoxy)ethylcarbamate, prepared as described in Example 1, and 10 mL of deionized water. The resulting slurry was heated to 50° C. After stirring at 50° C. for 1 h a clear solution was produced. This was allowed to cool and filtered through a Chromafil O-20/15 MS PTFE syringe filter into a clean 50 mL flask. The clear solution was evaporated using a rotary evaporator. Acetone (10 mL, HPLC grade, anhydrous) was added to the resulting colorless residue and the solvent was again removed. A second 10 mL portion of acetone was added to the residue and the mixture heated to reflux (bath temperature=67° C.). The residue dissolved on heating and a clear solution was produced. After refluxing for 30 min some white solids formed and the bath temperature was lowered to 25° C. Ethyl acetate (10 mL, HPLC grade, anhydrous) was added and the mixture stirred at 25° C. for 1 h. The crystals were collected on a piece of filter paper (Whatman No. 1) contained in a porcelain crucible filter. They were washed with additional ethyl acetate and allowed to air dry for ~30 min, then dried under vacuum for 17 h. $^1$H NMR (DMSO-$d_6$, 35° C.) showed a 2:1 salt with no excess mucic acid. The white crystals had a melting range of 133-136° C. The XRPD pattern for the obtained Formula (I) hemi mucate (Form D) product is shown in FIG. 4.

Methyl ethyl ketone can be used in place of acetone.

Example 7

X-Ray Powder Diffraction (XRPD) Measurements

XRPD patterns were determined for the crystalline forms of Formula (I) Mucic Acid Salts prepared in Examples 3-6 using the sample preparation, measuring conditions and data evaluation described in the following.

Sample Preparation:

The samples were generally prepared without any special treatment other than the application of slight pressure to get a flat surface. The salt of Example 4 was recorded using a single-crystal silicon sample holder that was 1-mm deep and held ~70 mg of sample. All other measurements (i.e., for Samples of Examples 3, 5, and 6) were recorded using single-crystal silicon sample holders that were 0.1-mm deep and held 5-20 mg of sample.

Measuring Conditions:

Bruker D8, reflection geometry with Bragg-Brentano configuration

Copper $K_\alpha$ radiation, 40 kV/40 mA

Variable divergence slit

Ni filter for diffracted beam

LynxEye detector with 3° window

Step size: 0.02° 2θ, step time: 37 s

The samples were rotated at 0.5 rps during the measurement.

Measurements were performed at room temperature (20° C. to 25° C.)

Data Evaluation:

The d-value analysis was performed with Bruker's EVA software, version 14, 0, 0, 0.

Cu $K_{2\alpha}$ was removed by the software.

Amorphous background was removed by the software thereby obtaining a processed diffractogram.

Only significant lines up to 35° 2θ were listed.

Relative peak intensities were classified as follows: very weak (<5%), weak (≧5% but <15%), medium (≧15% but <50%), strong (≧50% but <90%), and very strong (≧90%).

TABLE 1

Significant XRPD peaks for the Formula (I) Mucic Acid Salt of Example 3

| Angle 2-Theta ° | d value Angstrom | Intensity Cps | Relative Intensity % |
|---|---|---|---|
| 3.79 | 23.3 | m | 16 |
| 5.14 | 17.2 | m | 40 |
| 6.79 | 13.0 | m | 38 |
| 7.62 | 11.6 | s | 66 |
| 8.85 | 10.0 | w | 8 |
| 10.35 | 8.5 | m | 17 |
| 11.45 | 7.7 | w | 12 |
| 11.99 | 7.4 | m | 39 |
| 12.55 | 7.0 | m | 15 |
| 13.63 | 6.5 | m | 18 |
| 15.25 | 5.80 | m | 21 |
| 16.44 | 5.39 | s | 63 |
| 17.15 | 5.17 | s | 53 |
| 19.28 | 4.60 | m | 44 |
| 20.23 | 4.39 | vs | 100 |
| 22.98 | 3.87 | m | 29 |
| 24.07 | 3.70 | m | 18 |

The corresponding diffractogram is shown in FIG. 1 and the corresponding processed diffractogram is shown in FIG. 5.

TABLE 2

Significant XRPD peaks for the Formula (I) Mucic Acid Salt of Example 4

| Angle 2-Theta ° | d value Angstrom | Intensity Cps | Relative Intensity % |
|---|---|---|---|
| 3.79 | 23.3 | vw | 4 |
| 5.15 | 17.2 | m | 22 |
| 6.52 | 13.6 | w | 8 |
| 6.76 | 13.1 | m | 29 |
| 7.61 | 11.6 | m | 49 |
| 8.83 | 10.0 | w | 10 |
| 10.32 | 8.6 | w | 12 |
| 11.41 | 7.7 | w | 10 |
| 11.94 | 7.4 | m | 35 |
| 12.47 | 7.1 | m | 15 |
| 13.58 | 6.5 | m | 16 |
| 14.28 | 6.2 | w | 6 |
| 15.22 | 5.82 | m | 24 |
| 16.38 | 5.41 | s | 71 |
| 17.08 | 5.19 | s | 61 |
| 17.65 | 5.02 | w | 11 |
| 18.56 | 4.78 | w | 15 |
| 19.16 | 4.63 | m | 42 |
| 20.12 | 4.41 | vs | 100 |
| 21.40 | 4.15 | m | 24 |
| 22.88 | 3.88 | m | 36 |
| 24.00 | 3.71 | m | 23 |
| 25.28 | 3.52 | w | 10 |
| 26.07 | 3.42 | w | 9 |
| 30.69 | 2.91 | w | 7 |

The corresponding diffractogram is shown in FIG. 2 and the corresponding processed diffractogram is shown in FIG. 6.

TABLE 3

Significant XRPD peaks for the Formula (I) Mucic Acid Salt of Example 5

| Angle 2-Theta ° | d value Angstrom | Intensity Cps | Relative Intensity % |
|---|---|---|---|
| 3.48 | 25.4 | vs | 100 |
| 4.48 | 19.7 | m | 25 |
| 5.73 | 15.4 | m | 46 |
| 6.27 | 14.1 | m | 20 |

TABLE 3-continued

Significant XRPD peaks for the Formula
(I) Mucic Acid Salt of Example 5

| Angle 2-Theta ° | d value Angstrom | Intensity Cps | Relative Intensity % |
|---|---|---|---|
| 7.10 | 12.4 | m | 23 |
| 7.76 | 11.4 | m | 39 |
| 8.59 | 10.3 | w | 7 |
| 9.21 | 9.6 | w | 11 |
| 9.64 | 9.2 | m | 15 |
| 11.63 | 7.6 | m | 27 |
| 12.49 | 7.1 | m | 15 |
| 12.74 | 6.9 | w | 14 |
| 15.18 | 5.83 | m | 30 |
| 15.67 | 5.65 | m | 32 |
| 16.37 | 5.41 | m | 25 |
| 17.14 | 5.17 | s | 57 |
| 17.94 | 4.94 | m | 47 |
| 18.46 | 4.80 | s | 73 |
| 18.81 | 4.71 | s | 70 |
| 19.23 | 4.61 | s | 76 |
| 19.48 | 4.55 | s | 75 |
| 21.30 | 4.17 | s | 78 |
| 21.78 | 4.08 | s | 66 |
| 22.12 | 4.02 | s | 55 |
| 22.73 | 3.91 | s | 81 |
| 24.25 | 3.67 | m | 24 |
| 25.22 | 3.53 | m | 28 |
| 27.19 | 3.28 | m | 23 |
| 29.67 | 3.01 | m | 21 |

The corresponding diffractogram is shown in FIG. 3 and the corresponding processed diffractogram is shown in FIG. 7.

TABLE 4

Significant XRPD peaks for the Formula
(I) Mucic Acid Salt of Example 6

| Angle 2-Theta ° | d value Angstrom | Intensity Cps | Relative Intensity % |
|---|---|---|---|
| 2.96 | 29.8 | m | 18 |
| 4.27 | 20.7 | m | 31 |
| 5.17 | 17.1 | m | 36 |
| 5.90 | 15.0 | m | 21 |
| 6.57 | 13.4 | vs | 100 |
| 7.25 | 12.2 | m | 31 |
| 7.65 | 11.5 | s | 61 |
| 8.95 | 9.9 | w | 10 |
| 9.78 | 9.0 | w | 13 |
| 10.52 | 8.4 | w | 12 |
| 11.50 | 7.7 | m | 15 |
| 12.27 | 7.2 | m | 43 |
| 12.97 | 6.8 | m | 21 |
| 13.38 | 6.6 | w | 12 |
| 14.05 | 6.3 | w | 10 |
| 14.75 | 6.0 | m | 41 |
| 15.50 | 5.71 | m | 40 |
| 16.32 | 5.43 | m | 30 |
| 16.96 | 5.23 | s | 54 |
| 17.42 | 5.09 | m | 41 |
| 18.39 | 4.82 | m | 37 |
| 19.25 | 4.61 | s | 87 |
| 19.98 | 4.44 | m | 47 |
| 20.77 | 4.27 | s | 77 |
| 22.22 | 4.00 | m | 37 |
| 22.91 | 3.88 | m | 29 |
| 23.89 | 3.72 | m | 40 |
| 24.58 | 3.62 | m | 24 |
| 26.70 | 3.34 | m | 17 |
| 28.51 | 3.13 | w | 13 |

The corresponding diffractogram is shown in FIG. 4 and the corresponding processed diffractogram is shown in FIG. 8.

Example 8

Differential Scanning calorimetric (DSC) Measurements

DSC was performed using a TA Instruments differential scanning calorimeter Q2000. The Formula (I) Mucic Acid Salt samples of Examples 3, 5 and 6 were placed into an aluminum DSC pan, and the weight accurately recorded. The sample cell was heated under a nitrogen purge from 25° C. to 250° C. at 10° C./min. Indium metal was used as the calibration standard.

The DSC traces for samples of Examples 3, 5 and 6 are shown in FIGS. 9, 10 and 11, respectively.

Example 9

Thermal Gravimetric Analysis (TGA)

TGA was performed using a TA Instruments Q5000IR thermogravimetric analyzer. The Formula (I) Mucic Acid Salt samples of Examples 3, 5 and 6 were placed in an aluminum sample pan and inserted into the TG furnace. The furnace was heated under nitrogen from 37° C. to 350° C. at 10° C./min. Nickel and Alumel™ were used as the calibration standards.

The TGA traces for samples of Examples 3, 5 and 6 are shown in FIGS. 12, 13 and 14, respectively.

Example 10

Pharmacokinetics

IV formulations were prepared in 1% DMSO in sterile saline. PO formulations were prepared in 0.5% methylcellulose in water, unless otherwise indicated. After compound administration, plasma samples were obtained through 24 hours post-dosing from each animal using $K_2EDTA$ as the anticoagulant. Plasma samples were treated with two volumes of acetonitrile containing an internal standard (ritanserin). Samples were centrifuged at 4,000 rpm for 10 minutes at 25° C. Ten microliters of the supernatant was analyzed using LC/MS/MS. Standard curves are prepared for each species and range from 1.0 to 500 ng/mL The compound of Formula (I) and the internal standard were separated by reverse-phase HPLC using a gradient mobile phase and detected by +APCI monitoring the transitions m/z 525→327 (compound of Formula (I)) and m/z 478→193 (ritanserin).

| Salt Form | Dose (as salt) | Vehicle[a] | Species | $C_{max}$ (ng/mL) | $AUC_{0-t}$ (ng·h/mL) | $DNAUC_{0-t}$ (ng·h/mL) |
|---|---|---|---|---|---|---|
| Fumarate[b] | 10 mg/kg | 0.5% methylcellulose in water | Rat | 156 | 477 | 48 |
| Fumarate[b] | 1 mg/kg | 2% DMSO in water | Dog | 286 | 458 | 458 |
| Fumarate[b] | 2 mg/kg | 0.5% methylcellulose in water | Monkey | 145 | 381 | 191 |
| Tartrate[c,g] | 2 mg/kg | 0.5% methylcellulose in water | Dog | 438 | 1205 | 602 |
| Tartrate[c,g] | 3 mg/kg | 0.5% methylcellulose in water | Monkey | 202 | 849 | 283 |
| Pamoate[c,d] | 8 mg/kg | 0.5% methylcellulose in water | Rat | BQL[e] | BQL[e] | BQL[e] |
| Pamoate[c] | 8 mg/kg | PEG-400 | Rat | BQL[e] | BQL[e] | BQL[e] |
| Mucate[c,f] | 10 mg/kg | 0.5% methylcellulose in water | Rat | 238 | 681 | 68 |
| Mucate[c,f] | 2 mg/kg | 0.5% methylcellulose in water | Dog | 294 | 895 | 447 |
| Mucate[c,f] | 3 mg/kg | 0.5% methylcellulose in water | Monkey | 266 | 807 | 269 |

[a]All compounds were administered orally;
[b]Amorphous lyophilized solid;
[c]Crystalline material;
[d]Did not dissolve in vehicle; sonicated prior to administration;
[e]BQL = below limit of quantitation;
[f]Form B,
[g]obtained in low yield, poor physical properties.

Formula (I) Pamoate was prepared as described in WO 2008/036247 and showed no quantifiable in vivo bioavailability in rats. In contrast, Formula (I) Mucic Acid Salt (Form B) has been found to have good in vivo bioavailability in rat, dog and monkey.

Example 11

Formula (I) Pamoate has been found to have a water solubility of 0.125 mg/mL at 37° C.

Crystalline forms of Formula (I) Mucic Acid Salt, particularly, Form B, Form C and Form D have been found to have good water solubility, for example, a water solubility of 65±5 mg/mL has been found for the crystalline form Form B. Further, the above-mentioned crystalline forms have been found to be sufficiently non-hygroscopic Example 12

Preparation of methyl 2-((R)-(3-chlorophenyl)((R)-1-((S)-2-(methylamino)-3-((R)-tetrahydro-2H-pyran-3-yl)propylcarbamoyl)piperidin-3-yl)methoxy)ethylcarbamate fumaric acid salt A solution of methyl 2-((R)-(3-chlorophenyl)((R)-1-((S)-2-(methylamino)-3-((R)-tetrahydro-2H-pyran-3-yl)propylcarbamoyl)piperidin-3-yl)methoxy)ethylcarbamate TFA salt (389 mg, 0.625 mmol) (prepared as in WO 2008/036247) in ethyl acetate (100 mL) was washed with aqueous 1 M NaOH (3×30 mL), $H_2O$ (3×30 mL) and brine successively, and dried over anhydrous $Na_2SO_4$. The solvent was removed under reduced pressure after filtration to give 287 mg of free amine (yield 88%) as white foam. Fumaric acid (63 mg, 0.543 mmol) was added to the free amine, and the mixture was dissolved in EtOH (5 mL) to make a clear solution. The organic solvent was removed under reduced pressure. Deionized water (15 mL) was added to the residue to dissolve the fumarate salt. The resulting clear solution was cooled in a dry-ice/acetone bath with swirling until it froze. The flask was attached to a lyophilizer and freeze dried overnight to afford methyl 2-((R)-(3-chlorophenyl)((R)-1-((S)-2-(methylamino)-3-((R)-tetrahydro-2H-pyran-3-yl)propylcarbamoyl) piperidin-3-yl)methoxy)ethylcarbamate fumarate salt 316 mg. MS M/Z (ESI): 525 $(M+H)^+$; $^1H$ NMR (400 MHz, $CD_3OD$) δ (ppm): 7.37-7.30 (m, 3H), 7.20 (d, J=7.2 Hz, 1H), 6.71 (s, 2H), 4.22 (br d, J=13.2 Hz, 1H), 4.03 (d, J=8.8 Hz, 1H), 3.87-3.78 (m, 3H), 3.63 (s, 3H), 3.58 (m, 1H), 3.44 (td, J=10.4, 3.6 Hz, 1H), 3.37-3.23 (m, 4H), 3.16 (t, J=10.4 Hz, 1H), 2.95-2.86 (m, 2H), 2.75 (s, 3H), 1.99 (m, 1H), 1.80-1.75 (m, 2H), 1.70-1.61 (m, 3H), 1.53-1.48 (m, 2H), 1.37-1.25 (m, 3H), 1.67 (m, 1H).

While this invention has been particularly shown and described with references to example embodiments thereof, it will be understood by those skilled in the art that various changes in form and details may be made therein without departing from the scope of the invention encompassed by the appended claims.

What is claimed is:

1. A crystalline form of mucic acid salt of a compound represented by the following structural formula:

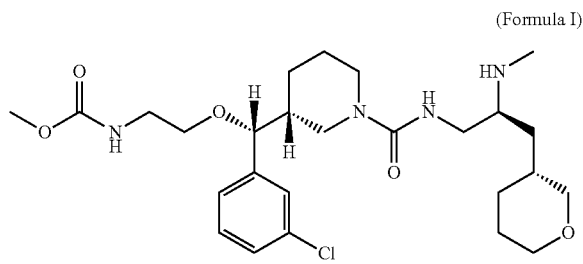 [SMILES: CN[C@H](CNC(=O)N1CCC[C@@H]([C@@H](OCCNC(=O)OC)c2cccc(Cl)c2)C1)C[C@H]1CCCOC1]

(Formula I)

wherein the crystalline form is selected from Form B as characterized by an x-ray diffraction pattern in accordance with FIG. 1 or FIG. 2, Form D as characterized by an x-ray diffraction pattern in accordance with FIG. 4, or a combination thereof.

2. The crystalline form of claim 1, wherein the salt is a hemi mucate salt.

3. The crystalline form of claim 2, wherein at least 50% by weight of the crystalline form is in a single crystalline form.

4. The crystalline form of claim 2, wherein at least 90% by weight of the crystalline form is a single crystalline form.

5. The crystalline form of claim 3 or 4, wherein the single crystalline form is Form B.

6. The crystalline form of claim 3 or 4, wherein the single crystalline form is Form D.

7. The crystalline form of claim 3 or 4, wherein the single crystalline form is characterized by at least three major x-ray powder diffraction peaks at 2θ angles selected from 7.61°, 16.38°, 17.08°, 19.16° and 20.12.

8. The crystalline form of claim 3 or 4, wherein the single crystalline form is characterized by the following major x-ray powder diffraction peaks at 2θ angles 7.61°, 16.38°, 17.08°, 19.16° and 20.12.

9. The crystalline form of claim 3 or 4, wherein the single crystalline form is characterized by x-ray powder diffraction peaks at 2θ angles of 3.79°, 5.15°, 6.76°, 7.61°, 8.83°, 10.32°, 11.41°, 11.94°, 12.47°, 13.58°, 15.22°, 16.38°, 17.08°, 19.16° and 20.12°.

10. The crystalline form of claim 3 or 4, wherein the single crystalline form is characterized by at least four major x-ray powder diffraction peaks at 2θ angles selected from 6.57°, 7.65°, 12.27°, 14.75°, 16.96°, 17.42°, 19.25°, 19.98°, and 20.77°.

11. The crystalline form of claim 3 or 4, wherein the single crystalline form is characterized by at least seven major x-ray powder diffraction peaks at 2θ angles selected from 6.57°, 7.65°, 12.27°, 14.75°, 16.96°, 17.42°, 19.25°, 19.98°, and 20.77°.

12. The crystalline form of claim 3 or 4, wherein the single crystalline form is characterized by the following major x-ray powder diffraction peaks at 2θ angles 6.57°, 7.65°, 12.27°, 14.75°, 16.96°, 17.42°, 19.25°, 19.98°, and 20.77°.

13. The crystalline form of claim 3 or 4, wherein the single crystalline form is characterized by x-ray powder diffraction peaks at 2θ angles of angles selected from 2.96°, 4.27°, 5.17°, 5.90°, 6.57°, 7.25°, 7.65°, 8.95°, 9.78°, 10.52°, 11.50°, 12.27°, 12.97°, 13.38°, 14.05°, 14.75°, 15.50°, 16.32°, 16.96°, 17.42°, 18.39°, 19.25°, 19.98°, 20.77°, 22.22°, 22.91°, 23.89°, 24.58°, 26.70°, and 28.51°.

14. A pharmaceutical composition comprising a crystalline form of mucic acid salt of a compound represented by the following structural formula:

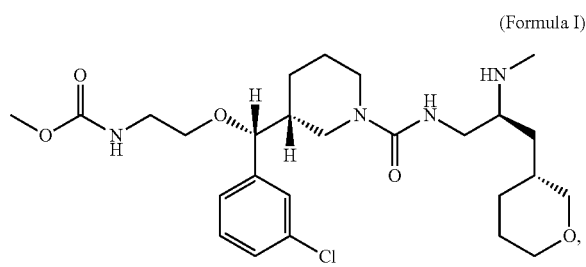 [SMILES: CN[C@H](CNC(=O)N1CCC[C@@H]([C@@H](OCCNC(=O)OC)c2cccc(Cl)c2)C1)C[C@H]1CCCOC1]

(Formula I)

wherein the crystalline form is selected from Form B as characterized by an x-ray diffraction pattern in accordance with FIG. 1 or FIG. 2, Form D characterized by an x-ray diffraction pattern in accordance with FIG. 4, or a combination thereof;

and a pharmaceutically acceptable carrier or diluent.

15. The pharmaceutical composition of claim 14, wherein the salt is a hemi mucate salt.

* * * * *